(12) United States Patent
Skrott et al.

(10) Patent No.: US 11,766,404 B2
(45) Date of Patent: Sep. 26, 2023

(54) BIOAVAILABLE DITHIOCARBAMATE-METAL COMPLEX PARTICLES, METHOD OF PREPARATION AND USE THEREOF

(71) Applicant: PALACKY UNIVERSITY OLOMOUC, Olomouc (CZ)

(72) Inventors: Zdenek Skrott, Ruzdka (CZ); Martin Mistrik, Olomouc (CZ); Marian Hajduch, Moravsky Beroun (CZ); Petr Dzubak, Brodek U Prerova (CZ); Jiri Bartek, Greve (DK); Radek Zboril, Olomouc (CZ)

(73) Assignee: PALACKY UNIVERSITY OLOMOUC, Olomouc (CZ)

( * ) Notice: Subject to any disclaimer, the term of this patent is extended or adjusted under 35 U.S.C. 154(b) by 0 days.

(21) Appl. No.: 16/649,947

(22) PCT Filed: Sep. 26, 2018

(86) PCT No.: PCT/EP2018/076098
§ 371 (c)(1),
(2) Date: Mar. 23, 2020

(87) PCT Pub. No.: WO2019/063601
PCT Pub. Date: Apr. 4, 2019

(65) Prior Publication Data
US 2020/0276124 A1 Sep. 3, 2020

(51) Int. Cl.
| | |
|---|---|
| *A61K 9/14* | (2006.01) |
| *A61K 31/325* | (2006.01) |
| *A61K 38/38* | (2006.01) |
| *A61K 51/12* | (2006.01) |
| *A61K 51/04* | (2006.01) |
| *A61K 9/19* | (2006.01) |

(52) U.S. Cl.
CPC ............ *A61K 9/145* (2013.01); *A61K 31/325* (2013.01); *A61K 38/385* (2013.01); *A61K 51/0478* (2013.01); *A61K 51/1244* (2013.01); *A61K 9/19* (2013.01)

(58) Field of Classification Search
CPC ...... A61K 31/325; A61K 38/38; A61K 51/12; A61K 51/04; A61K 9/14
See application file for complete search history.

(56) References Cited

U.S. PATENT DOCUMENTS

| | | | |
|---|---|---|---|
| 2003/0229064 A1 | 12/2003 | Kennedy | |
| 2005/0096304 A1 | 5/2005 | White et al. | |
| 2006/0040980 A1 | 2/2006 | Lind | |
| 2007/0269375 A1* | 11/2007 | Chen | A61K 51/088 514/561 |

FOREIGN PATENT DOCUMENTS

| | | |
|---|---|---|
| CN | 103222961 A | 7/2013 |
| EP | 1214063 A | 6/2002 |

OTHER PUBLICATIONS

International search report and written opinion for corresponding PCT application No. PCT/EP2018/076098, dated Dec. 3, 2018.

* cited by examiner

*Primary Examiner* — Genevieve S Alley
(74) *Attorney, Agent, or Firm* — Notaro, Michalos & Zaccaria P.C.

(57) ABSTRACT

A particulate form of dithiocarbamate-metal complex and at least one blood protein. The particulate form is obtained by a process having a sequential or simultaneous addition of individual components, resulting in their self-assembling. The aqueous dispersion of the particulate form is suitable for parenteral, oral and topical administration and for therapy and visualization of cancer.

38 Claims, 10 Drawing Sheets

Fig. 5a
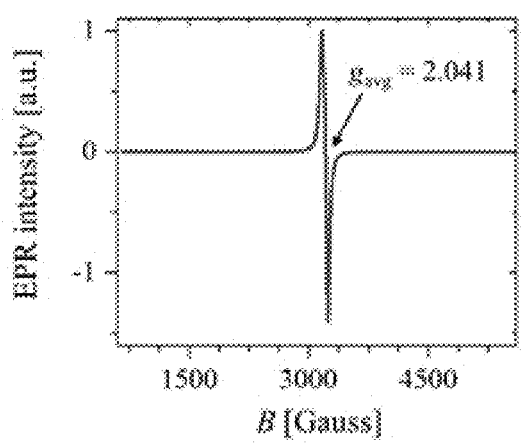
Fig. 5b
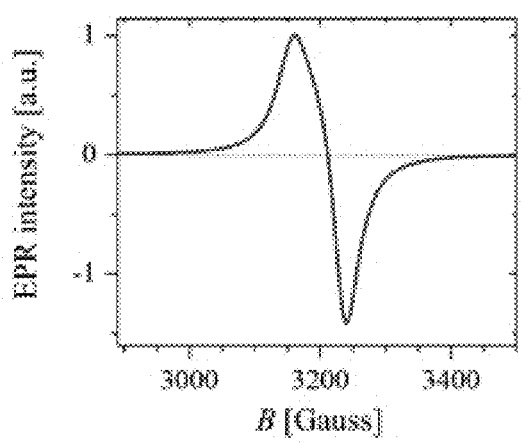
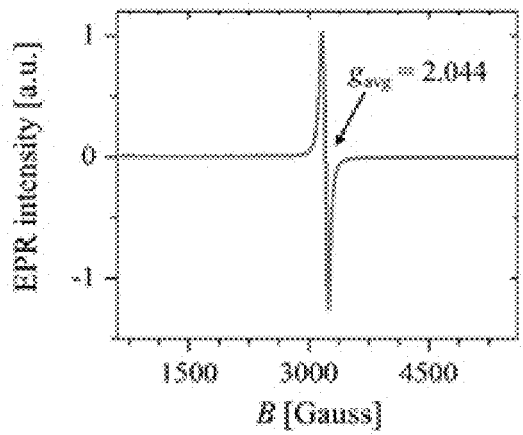
Fig. 5c
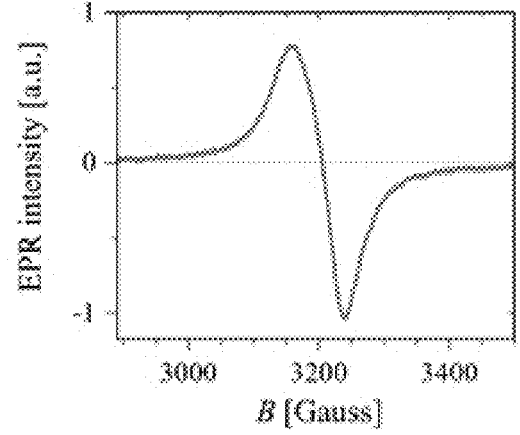
Fig. 5d

BIOAVAILABLE DITHIOCARBAMATE-METAL COMPLEX PARTICLES, METHOD OF PREPARATION AND USE THEREOF

FIELD OF THE INVENTION

The present invention relates to particles of R1,R2-dithiocarbamate-metal complex and blood serum protein or mixture of blood serum proteins, usable for obtaining antitumor compositions suitable for medical applications, including cancer treatment and diagnostics, as well as a process for producing such particles.

BACKGROUND ART

R1,R2-dithiocarbamates (DTC) are strong metal ion chelators known in literature. Once complex between DTC and metal is formed some of these complexes display anticancer activity in cellular systems employing various cancer cell models. However, the complexes with proposed antitumor activity are not water soluble, which makes it particularly difficult to administer such complex to patients; also the complexes show low preferential toxicity towards cancer cells and thus nearly narrow therapeutic index. Both limitations can be overcome by present invention.

Dithiocarbamates (DTC), particularly in complex with various bivalent metals, exhibit promising anticancer activity in various preclinical models. Metal chelating properties of DTC's are known for a long time, as well as their antitumor activity. Several patent documents have covered the use of dithiocarbamate complexes with heavy metals, especially with copper, zinc, gold or silver, as a treatment strategy for various malignancies (see e.g. US20030229064, US20050096304). However, none of these patent documents has been translated to practical use in humans so far. Apparently, the main obstacle for the use of dithiocarbamate-metal complexes in the clinical routine are unfavourable pharmacologic properties, namely stability and water based formulation capabilities. For instance, for the most promising anticancer complex which is bis(diethyldithiocarbamate) copper(II) (or copper bis(diethyldithiocarbamate)), the solubility constant in water is only in the range of nanograms per litre, which is insufficient to deliver therapeutic doses in patients.

SUMMARY OF THE INVENTION

The main object of the present invention is a novel particulate form of dithiocarbamate-metal complex and process for its preparation, such as in-situ preparation, in the form of bioavailable dispersion of particles directly usable as anticancer drug or as a diagnostic agent.

The particulate form comprises or consists of dithiocarbamate-metal complex and at least one blood protein, preferably at least one blood serum protein. The dithiocarbamate-metal complex and the blood protein are preferably in the form of a molecular assembly and/or have the size in the range of 2-900 nm. The particulate form is preferably substantially free of organic solvents.

The term "molecular assembly" refers to a molecular complex comprising the dithiocarbamate-metal complex and the at least one blood protein. The components of a molecular assembly are typically bound together by non-covalent interactions to form the molecular complex.

The structure of a molecular assembly is different from, e.g., core-shell particles, aggregates, mixtures, etc., in particular in that the molecular assembly contains the molecules of the components bound together by non-covalent binding interactions in a stoichiometric ratio.

The average size of the particles refers to Z-average size as measured by Dynamic Light Scattering (DLS). The Z-average is obtained from the DLS data by analysis using the technique of cumulants. The method of determining the Z-average size from DLS data is known to a skilled person. The Z-average size refers to hydrodynamic size.

Preferably, the particulate form comprises or consists of dithiocarbamate-copper complex and at least one blood protein, preferably at least one blood serum protein. The dithiocarbamate-metal complex and the blood protein are preferably in the form of molecular assembly and/or have the size in the range of 2-900 nm. The particulate form is preferably substantially free of organic solvents.

According to the present invention, the particulate form (herein also referred to as particles, preferably nanoparticles) is prepared by combining a first component selected from a dithiocarbamate and a metal salt with at least one blood protein in an aqueous solvent, and simultaneously or subsequently adding a second component selected from a dithiocarbamate and a metal salt, whereas if the first component is a dithiocarbamate, then the second component is a metal salt; and if the first component is a metal salt, then the second component is a dithiocarbamate.

Within the framework of the present invention, it was discovered that when the simultaneous or sequential addition of the reagents is carried out as described herein, then after the addition of the second component, the blood proteins have a considerable capacity to bind to the dithiocarbamate-metal complex that is rapidly formed in the solution and spontaneously assemble into particles, preferably having the average size within the range 2-900 nm, thus forming an injectable bioavailable dispersion of particles. In this particulate form the molecules of dithiocarbamate-metal complex, such as dithiocabamate-copper complex, are uniformly distributed, maintain their original chemical properties and exhibit a substantially improved biological activity, both in vitro and in vivo, thus enabling an unexpected pharmaceutical use of otherwise water-insoluble compound, including the use in cancer treatment and tumour visualization.

The process of particle preparation can be performed in a very short time (below 1 minute), even at the patient's bed, in a single reaction vessel without the need of organic (non-polar) solvents and which allows either immediate or sustained parenteral administration.

The present invention further includes a kit of parts comprising a dithiocarbamate, a metal salt, a sterile aqueous solvent wherein the aqueous solvent is preferably water or water-based buffer, and a container for combining the dithiocarbamate, the metal salt and at least one blood protein in the aqueous solvent under sterile conditions. The kit of parts may further contain at least one blood protein, preferably a substantially pure blood protein. The components of the kit may be provided in separate containers within the kit.

DETAILED DESCRIPTION OF THE INVENTION

In the present invention, "metal" means a metal selected from transition metals (or d-metals) and metals of the IIIA and IVA groups of the periodic table. Preferably, metals are transition metals. More preferably, the metal is selected from copper, zinc, cadmium, mercury. Most preferably, the metal is copper. All advantages of the present invention are most strongly pronounced for copper.

The metal may be in the form of a single isotope or an isotopic mixture. The isotopes may be radioactive isotopes or non-radioactive isotopes. For copper, non-radioactive isotopes are $^{63}$Cu and $^{65}$Cu, and radioactive isotopes are preferably $^{64}$Cu or $^{67}$Cu. $^{64}$Cu is a positron emitting isotope of copper, with applications for molecular radiotherapy and positron emission tomography.

"Metal salt" means a salt of the metal in the form of a cation with an anion. With regard to the intended pharmaceutical use of the particle dispersion, the skilled person would understand that the anion should be a pharmaceutically acceptable anion and preferably water-soluble. The anion may be selected, e.g. from inorganic acid anions such as halogenides (in particular chlorides, bromides, iodides), sulfates, sulfites, sulfides, phosphates, nitrates, carbonates; carboxylic acid anions, dicarboxylic acid anions, tricarboxylic acid anions, sulfonic acid anions, amino acid anions, such as formates, acetates, propionates, oxalates, succinates, maleinates, fumarates, maleates, citrates, triflates, gluconates, bis-glycinates.

"Dithiocarbamate" means a moiety having the formula (R1)(R2)N—CS$_2^-$ (also referred to in this text as R1,R2-dithiocarbamate), wherein R1 and R2 are the same or different and are independently selected from C1-C8 alkyl, C2-C8 alkenyl, C3-C10 cycloalkyl, C6-C14 aryl, C4-C14 heteroaryl containing at least one heteroatom selected from O, S, N, C3-C10 heterocyclyl containing at least one heteroatom selected from O, S, N; or R1 and R2 together with the nitrogen atom on which they are bound form a heterocycle, wherein —R1-R2- is a C2-C6 alkylene or a C2-C6 alkenylene, wherein optionally 1-2 carbon atoms may be replaced by heteroatoms selected from O, S, NH. The moieties forming R1 and R2 may be unsubstituted or further substituted by at least one substituent selected from C1-C4 alkyl, hydroxy, mercapto, C1-C4 alkoxy, C1-C4 alkylthio, halogen, phenyl, benzyl, keto group, carboxyl group, C1-C4 alkyloxycarbonyl.

More preferably, R1 and R2 are independently selected from C1-C6 (or C1-C4) alkyl, C2-C6 (or C2-C4) alkenyl, C3-C6 cycloalkyl, phenyl; or R1 and R2 together with the nitrogen atom on which they are bound form a heterocycle, wherein —R1-R2- is a C2-C6 alkylene or a C2-C6 alkenylene.

Most preferably, the dithiocarbamate is diethyldithiocarbamate (R1 and R2 are ethyl).

Dithiocarbamate can be present in the form of a negatively charged anion, typically in the dithiocarbamate-metal complex. As a starting compound in the process of the present invention, it may be used in the form of a neutral compound (R1)(R2)N—C(S)SH or, preferably, in the form of a salt [(R1)(R2)N—CS$_2$]$^{m-}$Cat$^{m+}$, such as alkali metal salt (Cat$^+$ is an alkali metal cation, m=1), ammonium salt (Cat$^+$ is an ammonium cation, m=1) or alkaline earth metal salt (Cat$^+$ is an alkaline earth metal cation, m=2). The skilled person understands which form is meant or which form is necessary, depending on the context in which the term "dithiocarbamate" is used.

"Dithiocarbamate-metal complex" is a complex comprising at least one dithiocarbamate moiety and at least one metal, preferably one metal. For example, the dithiocarbamate-metal complex may correspond to formula (I)

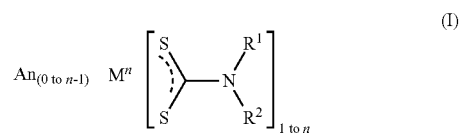

wherein
M is a metal, preferably copper,
An is a pharmaceutically acceptable anion, preferably as defined herein above,
n is the valence of the d-metal, typically, n is 1, 2, or 3, and R1 and R2 are as defined herein above.

The ratio of the metal to dithiocarbamate may be for example in the range of from 1:5 to 5:1, or in the range of 1:2 to 5:1. The ratio of the metal to dithiocarbamate may optimally correspond to their stoichiometric ratio in the complex, or to their stoichiometric ratio±20%, or to their stechiometric ratio±50%. For example, for copper the stoichiometric ratio is 2:1.

"Blood protein" means a protein which is naturally present in blood of an animal, including a human. The blood protein is preferably a "blood serum protein" which means a protein which is naturally present in blood serum of an animal, including a human. Preferably, the present invention uses human blood proteins or human blood serum proteins, but also blood proteins or blood serum proteins of other animals, preferably mammals, can be used, such as dog, cat, horse, mouse, rat, rabbit, goat, sheep, cattle blood proteins or blood serum proteins. The blood proteins or blood serum proteins may be isolated from blood or blood serum, respectively, or may be of recombinant origin.

The blood proteins, or more particularly the blood serum proteins, may be in the form of substantially pure proteins or in the form of a mixture of proteins.

The blood serum proteins are preferably selected from the group comprising albumin, transferrin, immunoglobulin, ceruloplasmin, and mixtures comprising these proteins. Most, preferably, the blood serum protein is albumin. In some preferred embodiments, the blood serum protein is an immunoglobulin.

"At least one blood protein" means one or a plurality of blood proteins. Therefore, the reaction mixture in the process of the present invention and/or the particles of the present invention may comprise one blood protein or a mixture of blood proteins. The mixture of blood proteins may be, e.g., whole blood, blood plasma or blood serum, or an artificially prepared mixture of at least two blood proteins.

"At least one blood serum protein" means one or a plurality of blood serum proteins. Therefore, the reaction mixture in the process of the present invention and/or the particles of the present invention may comprise one blood serum protein or a mixture of blood serum proteins. The mixture of blood serum proteins may be, e.g., whole blood, blood plasma or blood serum, or an artificially prepared mixture of at least two blood serum proteins.

The particulate molecular assemblies are in some embodiments in the form of a suspension or dispersion in an aqueous solvent. In some embodiments, they are provided in lyophilized or dried form.

"Aqueous solvent" is water or a water-based buffer, such as phosphate, citrate, acetate, Tris, HEPES, saline or other common buffers. Preferably, the aqueous solvent is sterile.

The size of the self-assembled particles (i.e., molecular assemblies) is 2-900 nm. Preferably, at least 90% of the particles have the size within the range of 2-500 nm. In some embodiments, at least 50%, or at least 70%, or at least 90% of the particles have the size within the range of 2-100 nm, or within the range of 10-100 nm, or within the range of 2 to 90 nm, or within the range of 2 to 80 nm, or within the range of 2-220 nm, or within the range of 2-200 nm, or within the range of 10-200 nm. The particle sizes and their distributions were measured by Dynamic Light Scattering (DLS) method and the term "size" or "average size" as used throughout this text refers to the average size as determined by DLS.

The particulate molecular assemblies of the present invention preferably have a negative zeta-potential. More preferably, they have a zeta-potential lower than −15 mV (=more negative than −15 mV). Even more preferably, they have a zeta-potential lower than −20 mV, or lower than −30 mV.

The particulate form consisting of or comprising dithiocarbamate-metal complex and at least one blood protein may be filter sterilized (sterile filtered), preferably using a 0.22 micrometer filter.

The particulate form consisting of or comprising dithiocarbamate-metal complex and at least one blood protein may be provided in the form of an injection or infusion liquid (solution, dispersion or suspension), drops, spray, instillation, suppository, capsule, tablet, ointment, lotion or cream. The pharmaceutical formulation further comprises at least one pharmaceutically acceptable excipients and/or ingredients selected from buffers, surfactants, chelating agents, isotonicity adjustment agents, pH adjustment agents, preservatives, stabilisers, antioxidants, reducing agents, solubilizers, metal ions, binders, glidants, lubricants, diluents, disintegrants, sweeteners, flavours, coating polymers, emulsion components, ointment bases or cream bases.

The particulate form consisting of or comprising dithiocarbamate-metal complex and at least one blood protein may be provided in a dry form, in particular in a lyophilized (freeze-dried) form or in a spray-dried form. The lyophilized formulation typically further comprises at least one pharmaceutically acceptable excipients selected from cryoprotectants, buffers, surfactants, chelating agents, isotonicity adjustment agents, pH adjustment agents, preservatives, stabilisers, antioxidants, reducing agents, solubilizers, metal ions. The spray-dried formulation may further comprise at least one pharmaceutically acceptable excipients selected from buffers, surfactants, chelating agents, isotonicity adjustment agents, pH adjustment agents, preservatives, stabilisers, antioxidants, reducing agents, solubilizers, metal ions. In particular, lyophilization further improves stability, and thus facilitates storage and logistics. Lyophilized particulate form may be used in particular in powders, capsules, tablets, ointments, lotions or creams, as well as for preparation of injection liquids, infusion liquids and other liquid pharmaceutical forms by resuspension.

The buffers may include acetate, succinate, citrate, triethanolamine, arginine, phosphate buffers.

The surfactants may be, e.g., polysorbate 80, polysorbate 20, poloxamer 188, poloxamer 407.

The chelating agents may include sodium edetate, glutamic acid, aspartic acid.

The isotonicity adjustment agents may be selected, e.g., from mannitol, sodium or potassium chloride, sorbitol, dextrose.

The pH adjustment agents may be, e.g., acetic acid, hydrochlorid acid.

The stabilizers may include arginine, methionine, glutamic acid, glycine, leucine, aspartic acid, fatty acids, phosphatidyl choline, ethanolamine, acetyltryptophanate, PEG, PVP (10, 24, 40), sorbitol, glucose, propylene glycol, ethylene glycol.

The antioxidants may include glycerin, ascorbic acid, cysteine HCl, thioglycerol, thioglycolic acid, thiosorbitol, glutathione, alpha tocopherol, sodium disulfide.

The reducing agents are, e.g., thiols.

The solubilizer may be, e.g., alanine.

The metal ions may include $Ca^{2+}$, $Ni^{2+}$, $Mg^{2+}$, $Mn^{2+}$.

The preservatives may include phenol, benzyl alcohol, chlorobutanol, metacresol and parabens.

Cryoprotectants (or lyoprotectants) may include monosaccharides, disaccharides, amino acids, polysaccharides polymers and other substances with cryoprotective properties, and derivatives thereof, in particular selected from mannitol, trehalose, saccharose, albumin, lactose, dextrose, sucrose, glucose, maltose, inositol, raffinose, inulin, maltodextrin, polysaccharides, heparin, 2-hydroxypropyl-β-cyclodextrin, glycerol, inositol, sorbitol, mercaptans, polyethylene glycol, adonitol, amino acids, polyoxyethylene sorbitan fatty acid esters (e.g. Tween 80), polyoxyethylene-polyoxypropylene copolymer (e.g. Pluronic), polyoxyethylene alkyl ethers (e.g. Brij), sodium dodecyl sulfate, ascorbic acid, polyvinylpyrrolidone (PVP K15), dextran.

The binders may include microcrystalline cellulose, polyvinylpyrrolidone, pregelatinised starch, lactose, fructose, mannitol, sorbitol, calcium sulphate, calcium hydrogenphosphate.

The glidants may include magnesium stearate, colloidal silicon dioxide, starch, talc.

The lubricants may include calcium silicate, calcium stearate, magnesium stearate, stearic acid, polyethylene glycol, polyoxyl stearate, polysorbate, sodium fatty acid sulfate, sorbitan fatty acid esters, talc.

The diluents may include lactose, microcrystalline cellulose, mannitol, sodium hydrogencarbonate.

The disintegrants may include crosslinked polyvinylpyrrolidone, croscarmellose sodium, modified starch sodium starch glycolate.

The coating polymers include cellulose ethers such as methylcellulose, hydroxymethylcellulose, ethylcellulose, hydroxypropylcellulose, hydroxypropyl methylcellulose phthalate; acrylic polymers such as methacrylic acid copolymers, methacrylate aminoester copolymer and other methacrylate ester copolymers; cellulose acetate phthalate, polyvinyl acetate phthalate, shellac, cellulose acetate trimellitate.

The nanoparticulate form, optionally with pharmaceutically acceptable excipients, may be administered to a subject in need of the treatment in any suitable manner, in particular parenterally, orally or topically.

The percentages, unless indicated otherwise, are w/v %.

The present invention describes the process of in-situ self-assembly of dithiocarbamate-copper complex and at least one blood protein into a nanoparticle. This is attained by a process comprising the steps of:

(a) solubilizing at least one blood protein in an aqueous solvent (e.g. water or water-based buffer) to a concentration in the range from 0.01% (w/v) to saturated solution (preferably from 0.1% to 10% (w/v)), or providing whole blood or blood plasma or blood serum of a patient;

(b) adding at least one dithiocarbamate dissolved in an aqueous solvent (e.g. water or water-based buffer) to a concentration in the range from 1 uM to 100 mM, preferably 1 to 10 mM;

(c) adding a metal salt solution in an aqueous solvent (e.g. water or water-based buffer), having the metal salt concentration in the range from 1 uM to 100 M, preferably 1 to 10 mM, wherein the steps are carried out in the sequence (a), (b), (c) or in the sequence (a), (c), (b), or steps (b) and (c) are carried out simultaneously.

Preferably, at least 10 second-delay accompanied by shaking or vortexing is made between individual steps.

This single-tube reaction leads to rapid spontaneous self-assembly of protein-dithiocarbamate-copper nanoparticulate form forming a dispersion of nanoparticles.

In step (a), blood proteins, preferably blood serum proteins such as albumin, transferrin, immunoglobulin, or mixtures thereof; or blood serum or blood plasma or whole blood may be used. It may be advantageous to use blood serum or blood plasma or whole blood taken from the patient who is to receive the final product.

Step (a) is preferably performed at a temperature in the range from 10 to 45° C., preferably 20 to 38° C., and/or at pH in the range from 5 to 8, most preferably 6.8.

In step (b), the dithiocarbamate is preferably in the form of a neutral compound or a salt.

In a preferred embodiment, the molar ratio of metal ions:dithiocarbamate ions is 1:2.

The use of aqueous solvents yields the nanoparticulate form which is biologically compatible, without the need for further purification. If organic solvents would be used, which could be preferred for dissolving dithiocarbamate, the resulting nanoparticles form core-shell structure (not a molecular assembly structure), contain residual amounts of the organic solvents which are difficult to remove. This decreases the biocompatibility, safety and bioavailability of the nanoparticles. Additionally, the use of organic solvents is known to lead to denaturation and modification of the blood protein, and this may result in altered protein structure, increased immunogenicity and lead to strong undesired immune system reaction due to the changes in the blood protein structure caused by modification, denaturation or partial denaturation. Thus, within the framework of the present invention, it was surprisingly found that when the method of preparation is carried out in aqueous solvents, a nanoparticulate form with a molecular assembly structure is formed, although dithiocarbamate has a low solubility in water. The use of aqueous solvents removes the disadvantages, which would be due to the use of organic solvents.

The nanoparticles of the present invention form a bioavailable dispersion of nanoparticles, and can be administered to a patient in need of such treatment. The dispersion of nanoparticles can be used in therapy, in particular cancer therapy, including chemotherapy, radiotherapy, immunotherapy, tumour treating fields therapy, thermotherapy, such as therapy of solid tumors including melanoma, non-small cell lung cancer, small cell lung cancer, renal cancer, colorectal cancer, breast cancer, pancreatic cancer, gastric cancer, bladder cancer, ovarian cancer, uterine cancer, lymphoma, prostate cancer, adenocarcinoma of the colon and nodal or hepatic metastases, brain metastases of solid and haematological cancers, multiple myeloma, glioblastoma. Preferably, the cancers to be treated are selected from brain metastases of solid tumours, multiple myeloma, glioblastoma and pancreatic cancer. The dispersion of nanoparticles can also be used in diagnostics, such as tumour visualisation, e.g., by positron emission tomography, single photon emission tomography, etc.

It is important to note that in case the reaction is performed according to the present invention the resulting dispersion of protein-dithiocarbamate-copper nanoparticles allows direct parenteral, oral or topical applications to the treated subject (human or animal) without the need of additional chemical or physical processing such as extractions, separations, product cleaning, concentration enhancement etc.

The particulate form for therapeutic use according to the present invention may preferably be administered to the treated subject so that the concentration of the CuET in blood after 1 hour of injection administration is at least 1 ng/l or wherein the concentration of the CuET in blood during infusion administration is at least 5 ng/l.

Moreover, the reaction of the present invention can be performed directly at the bed of the patient or in the hospital pharmacy using a combination of pharmaceutically acceptable ingredients. For example human serum albumin solution, diethyldithiocarbamate and $CuCl_2$ are commonly commercially available in pharmaceutical grades. Such procedure does not require costly chemical reactors, processing in additional devices and may simplify regulatory approval. In addition, it significantly limits some of the logistic problems related to the storage of the dispersion of nanoparticles—a fresh drug can be prepared with high reproducibility and immediately applied.

The present invention also enables simple modification of the size of assembled nanoparticles. By changing the ratio between dithiocarbamate-metal (in particular copper) complex and proteins, the formed nanoparticles are of different size following a rule that a higher protein concentration leads to smaller particles. Optimum reaction conditions can be determined to produce nanoparticles with the optimum pharmacologic properties, as the size of nanoparticles is important determinant of its behaviour in-vivo, in particular for biodistribution (e.g. blood-brain barrier penetration) and kinetics. The size of manufactured nanoparticles also depends on the substituents R1, R2 of the dithiocarbamate entering into the reaction. For example, dimethylditihiocarbamate with albumin forms larger particles compared to pyrrolidinedithiocarbamate with albumin despite all the other conditions of the two reactions being identical, suggesting smaller particles formation with longer R1, R2 groups.

The prepared dispersion of nanoparticles is relatively stable and can be stored for several months at 4° C. without significant degradation or precipitation. The formed nanoparticles of protein-dithiocarbamate-metal can be further processed by drying or lyophilisation to further improve stability, storage and logistics. Dried nanoparticles can be repeatedly dissolved in sterile water-based buffers and used for therapy. This important aspect of the protein-dithiocarbamate-metal nanoparticles properties is particularly valuable for both large- or small-scale industrial production, storage and logistics.

As immunoglobulin or immunoglobulin-containing mixtures can be used in the production of the nanoparticles, the resulting nanoparticles may harbour antibodies (or antibody fragments) against specific tumour or tissue antigens. This approach enables specific targeting of the nanoparticle into the tumour/tissue, yielding a better anticancer effect and a reduced systemic toxicity.

To prove general applicability of the particles, the following examples show preparation and characterization of dithiocarbamate-metal complex nanoparticles with blood proteins including albumin, transferrin and immunogblobulins alone or in combinations to demonstrate generic formulation and cancer targeting and tumour visualization capabilities of the resulting dispersion of nanoparticles. The examples should not be construed as limiting the scope of the claimed invention.

BRIEF DESCRIPTION OF DRAWINGS

FIGS. 5a-d show X-band electron paramagnetic resonance (EPR) spectra of bis(diethyldithiocarbamate) copper complex (CuET); FIGS. 5a-b are the resonances for the neat CuET powder obtained from TOKYO CHEMICAL INDUSTRY CO., LTD.; FIGS. 5c-d, are the resonances for the CuET-albumin nanoparticles prepared according to Example 1). The estimated $g_{avg}$-value of 2.044 and the overall resonance profile clearly indicate that upon nanoparticle formation no modification of the copper oxidation-state, and no substantial alteration of the Cu octahedral-field occur.

EXAMPLES

Materials and Methods

Figure 1:
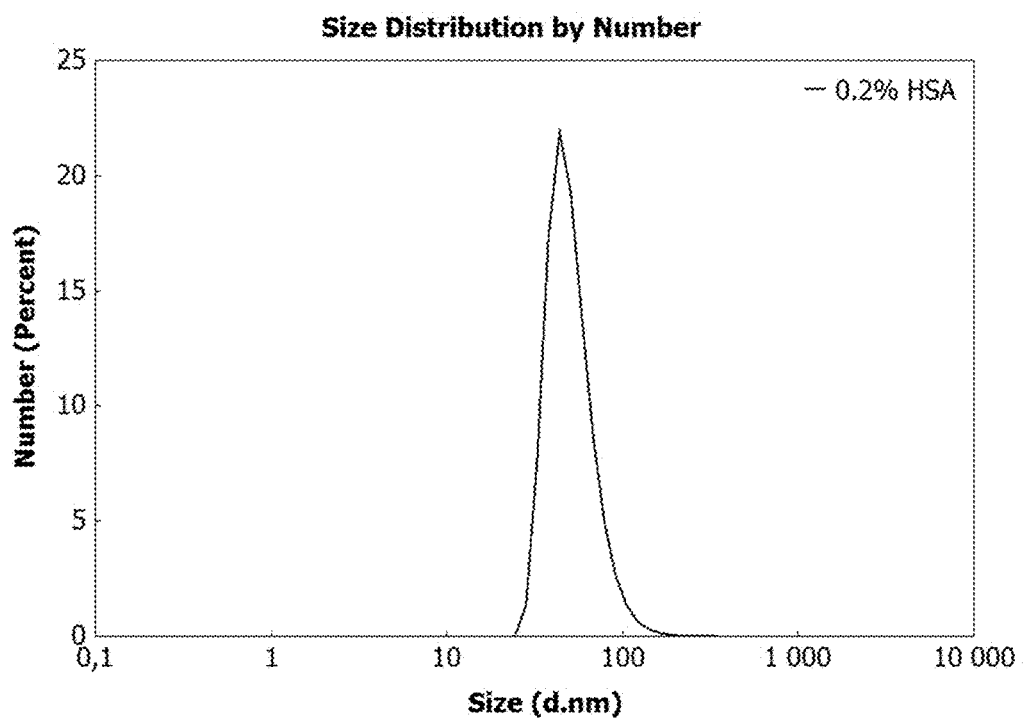
FIG. 1 shows dynamic light scattering (DLS) spectra of the nanoparticles prepared in Example 1. The nanoparticles form a polydispersed system: ca 20-100 nm; largest fraction: 30-40 nm.

Dynamic Light Scattering (DLS) analyses allowing to determine the average size and size distribution of the prepared nanoparticles were performed by the Zetasizer Nano ZS instrument (Malvern, U.K.), with following parameters setting: V=400 uL, T=25° C., Number of runs: 10, Run duration: is, Number of measurements: 3, Measurement angle: 173° Backscatter (NIBS default), Cell type: ZEN0040.

Transmission Electron Microcopy (TEM) images were obtained with TEM JEOL 2010 instrument with LaB6 type emission gun, operating at 100 kV. The analysis of crystal structure/amorphicity of nanoparticles is allowed with Selected Area Electron Diffraction (SAED) analysis. STEM/HAADF (Scanning Transmission Electron Microscopy/High-Angle Annular Dark-Field) analyses for EDS (Energy Dispersive X-ray Spectroscopy) mapping of elemental composition of nanoparticles were performed with a FEI Titan G2 HRTEM microscope operating at 80 kV. For STEM measurements, Super-X system with four silicon drift detectors (Bruker) was used. For all these microscopic analyses, a droplet of dispersion containing nanoparticles was deposited on a carbon-coated copper grid and slowly dried at room temperature.

Atomic Force Microscopy (AFM) images were taken by scanning tunnelling microscope Ntegra (Nt-MDT company) in the semi-contact AFM mode. The sample was scanned with Ha-NC tip. For the sample preparation, one drop of the dispersion containing nanoparticles was placed on the mica support and dried at room temperature.

Electron Paramagnetic Resonance (EPR) spectra of the frozen dispersion of nanoparticles were recorded at 140 K on JEOL JES-X-320 instrument operating at X-band frequency (9.17 GHz), equipped with a variable temperature control ES 13060DVT5 apparatus. High purity quartz tubes were employed (Suprasil, Wilmad, ≤0.5 OD). Other experimental parameters: 100 KHz modulation frequency, 0.1 mW microwave power, 0.03 s time constant, 8 Gauss modulation width.

Cell Lines

Cell lines were cultured in appropriate medium supplemented with 10% fetal bovine serum and penicillin/streptomycin; and maintained at humidified, 5% CO2 atmosphere at 37° C. Lines cultured in DMEM medium were: HCT116 (obtained from American Type Culture Collection, ATCC), DU145 (obtained from European Collection of Authenticated Cell Cultures, ECACC), MDA-MB-231 (ATCC), U-2-OS (ECACC), HeLa (ATCC), CAPAN-1 (ATCC), A253 (ATCC), FaDu (ATCC), h-TERT-RPE1 (ATCC). Cell lines cultured in RPMI1640 medium were: AMO-1 (ATCC), MM-1S (ATCC), OVCAR-3 (NCI60), CCRF-CEM (ATCC), K562 (ATCC), 786-0 (NCI60). Cell lines cultured in EMEM medium were: U87-MG (ATCC), SiHA (ATCC). Cell line A549 (ATCC) was cultured in F12K medium, HT29 (ATCC) in McCoy's medium. RWPE-1 (ATCC) cells were cultured in a keratinocyte serum-free medium supplemented with the bovine pituitary extract and human recombinant epidermal growth factor (Thermo Scientific).

Cell Viability Test

Cell viability was measured by XTT test. 10000 cells were seeded to 96-well plate. Next day the cells were treated as indicated. After 24 hours XTT assay was performed according manufacturer instructions (Applichem). XTT solution was added to media and incubated for 30-60 minutes, and then dye intensity was measured at 475 nm wavelength using spectrometer (TECAN, Infinite M200PRO). Results are shown as mean values and standard deviations from 3 independent experiments, each performed in 3 replicates. For LD50 (lethal dose) analysis across panel of cell lines listed in Extended data 2d, cell lines were treated with various doses (at least 5 doses) for 48 hours. LD50s are calculated using Graphpad Prism software based on survival curves from at least two independent experiments.

Sample preparation for HPLC/MS analysis of CuET pharmacokinetics and/or tissue distribution Liquid nitrogen-frozen biological samples (brain tissue) were cut into small pieces by scalpel. Sample (30-100 mg) was immediately processed by homogenization in 100% acetone in ratio 1:10 sample vs. acetone (for plasma or serum the ratio was 1:4). Homogenization was done in a table homogenizer (Retsch MM301) placed in a cold room (4° C.) in 2 ml Eppendorf tube with 2 glass balls (5 mm) for 1 min, 30 Hz. Next, tube was immediately centrifuged at 4° C., 20.000 G, 2 min. Supernatant was decanted into a new 1.5 ml Eppendorf tube and immediately centrifuged for 30 min using small table centrifuge (BioSan FVL-2400N) placed inside a −80° C. freezer. Supernatant was quickly decanted into glass HPLC vial and kept at −80° C. not longer than 6 hours. Just before the HPLC analysis the vial was placed into the pre-cooled (4° C.) LC-sample rack and immediately analyzed. Serum samples from pharmacokinetic analysis were processed similarly, but without homogenization. To enable quantification of analyzed CuET, calibration curve was prepared. Standards were then processed similarly as the samples described above.

HPLC-MS Detection of Copper-Diethyldithiocarbamate Complex

The copper-diethyldithiocarbamate analysis was performed on HPLC-ESI-QTOF system consisting of HPLC chromatograph Thermo UltiMate 3000 with AB Sciex TripleTOF 5600+ mass spectrometer, using the DuoSpray ESI. Data were acquired in Product ion mode with two parent masses 358.9 and 360.9 for analysis of CuET. Chromatographic separation was done by PTFE column especially designed for analysis of strong metal chelators filled by C18 sorbent (IntellMed, cat.no.IM_301). Analysis was performed at room temperature and flow rate 1500 µL/min with isocratic chromatography. Mobile phase consist of HPLC grade acetone (Lachner) 99.9%, HPLC water (Merck Millipore) 0.1% and 0.03% HPLC formic acid (Sigma). Acquired mass spectra were evaluated in software PeakView 1.2, where extracted ion chromatograms of transitions 88.0 and 116.0 (common for both parent masses) with 0.1 mass tolerance was Gaussian smoothened with width of 2 points.

PET Imaging

The presence of the $^{64}$Cu radioisotope in the tumours was visualised by combined positron emission tomography combined with computer tomography (PET/CT) imaging in severe combined immunodeficiency (SCID) mouse bearing MDA-MB-231 xenografts. The PET signal was collected 22 hours after the retro-orbital injection of dispersion of nanoparticles of MSA-diethyl-dithiocarbamate-copper$^{64}$ nanoparticles and dispersion of nanoparticles of human trans-ferrin-diethyl-dithiocarbamate-copper$^{64}$ nanoparticles corresponding to activity 33 MBq and 29 MBq, respectively. Signal was recorded using Albira PET/SPECT/CT imaging system (Bruker Biospin Corporation, Woodbridge, Conn., USA).

Mice In-Vivo Experiments

To test directly effect of CuET-albumin nanoparticles we used MDA-MB-231 and AMO1 models. MDA-MB-231 was injected (5*10$^6$ cells were transplanted s.c.) to grow tumours in SCID mice (Anlab, CZ). Similarly, the AMO-1 xenografts were expanded in SCID mice. Each group consisted of 10 animals, each bearing two tumours. CuET was formulated as nanoparticulate system in mouse serum albumin according to Example 12 or as the neat CuET powder (obtained from TOKYO CHEMICAL INDUSTRY CO., LTD.) dissolved in olive oil which is a standard formulation for non-polar compounds applied intraperitoneally in the mice experiments to final concentration 1 mg/ml. Olive oil alone and mouse serum albumin solutions were used as the vehicle controls. All solutions were applied intraperitoneally in a schedule 5 days ON and 2 days OFF, the CuET was applied in the final dose 1 mg per kg of body weight. All aspects of the animal studies met the accepted criteria for the care and experimental use of laboratory animals.

Protein Identification Using HPLC-MS

Acetone precipitated proteins were dissolved in the digestion buffer (8 M urea, 0.5 ammonium bicarbonate, pH=8) to a protein concentration of 1-5 µg/µl). Proteins in the sample were treated with dithiothreitol for reduction for 30 min at 56° C. and followed by iodoacetamide for alkylation for 30 min at room temperature in the dark. Sample was diluted to 0.8 M urea with 50 mM ammonium bicarbonate buffer and proteins were digested with trypsin (1/60) at 37° C. overnight. Digestion was stopped by adding TFA (pH=2). The peptides were purified by using C18 column. The sample was measured using LC-MS consisting of a Dionex Ulti-Mate 3000 RSLCnano system (Thermo Fisher Scientific) coupled via an EASY-spray ion source (Thermo Fisher Scientific) to an Orbitrap Elite mass spectrometer (Thermo Fisher Scientific). Purified peptides were separated on 50 cm EASY-Spray column (75 m ID, PepMap C18, 2 m particles, 100 Å pore size; Thermo Fisher Scientific). For each LC-MS/MS analysis, about 1 µg peptides were used for 165 min runs. First 5 min, peptides were loaded onto 2 cm trap column (Acclaim PepMap 100, 100 m ID, C18, 5 m particles, 100 Å pore size; Thermo Fisher Scientific) in loading buffer (98.9%/1%/0.1%, v/v/v, water/acetonitrile/formic acid) at a flow rate of 6 l/min. Thereafter has been switched valve and peptides were loaded in buffer A (99.9%/0.1%, v/v, water/formic acid) and eluted from EASY-Spray column with a linear 120 min gradient of 2%-35% of buffer B (99.9%/0.1%, v/v, acetonitrile/formic acid), followed by a 5 min 90% B wash at a flow rate 300 nl/min. EASY-Spray column temperature was kept at 35° C. Mass spectrometry data were acquired with a Top12 data-dependent MS/MS scan method. Target values for the full scan MS spectra were 1×106 charges in the 300-1700 m/z range, with a maximum injection time of 35 ms and resolution of 120,000 at m/z 400. The 2 m/z isolation window was used for MS/MS scans. Fragmentation of precursor ions was performed by CID dissociation with a normalized collision energy of 35. MS/MS scans were performed in ion trap with ion target value of 1×104 and maximum injection time of 100 ms. Dynamic exclusion was set to 70 s to avoid repeated sequencing of identical peptides.

Protein Data Analysis

Mass spectrometry raw files were analysed using the MaxQuant software environment (version 1.5.6.5), and its built-in Andromeda search engine. Proteins were identified by searching MS and MS/MS data against the human proteome from UniProtKB (UP000005640, January 2017) and common contaminants database. Carbamidomethylation of cysteines was set as a fixed modification. N-terminal acetylation and oxidation of methionines were set as variable modification. Trypsin was set as protease, and a maximum of two missed cleavages were allowed in the database search. Peptide identification was performed with an allowed initial precursor mass deviation up to 7 ppm (Orbitrap) and an allowed fragment mass deviation of 0.5 Da (collision-induced dissociation, ion trap). The "matching between runs" option was enabled to match identifications across samples within a time window of 20 s of the aligned retention times. The false discovery rate was set to 0.01 for both proteins and peptides with a minimum length of seven amino. LFQ was performed with a minimum ratio count of 2. Protein abundances were calculated on the basis of summed peptide intensities of unique and "razor" peptide. Protein matching to the reverse database and proteins identified only with modified peptides were filtered out.

Example 1

Preparation of Dispersion of Nanoparticles from 0.2% Human Serum Albumin (HSA) and Diethyldithiocarbamate and Copper Chloride Salt.

Procedure:

An injectable aqueous 20% (w/v) HSA solution in accordance with FDA specifications (pH=6.9±0.5) is diluted to 0.2% (w/v) with sterile water for injections. Sterile solution of diethyldithiocarbamate sodium salt (DTC) solubilised in water of a concentration 280 mM is added to 0.2% HSA to final concentration 5.6 mM, followed by brief stirring. To the 0.2% HSA solution containing 5.6 mM DTC is added sterile copper (ii) chloride (1 M concentration in water) to final concentration 2.8 mM, followed by brief stirring.

Figure 2:
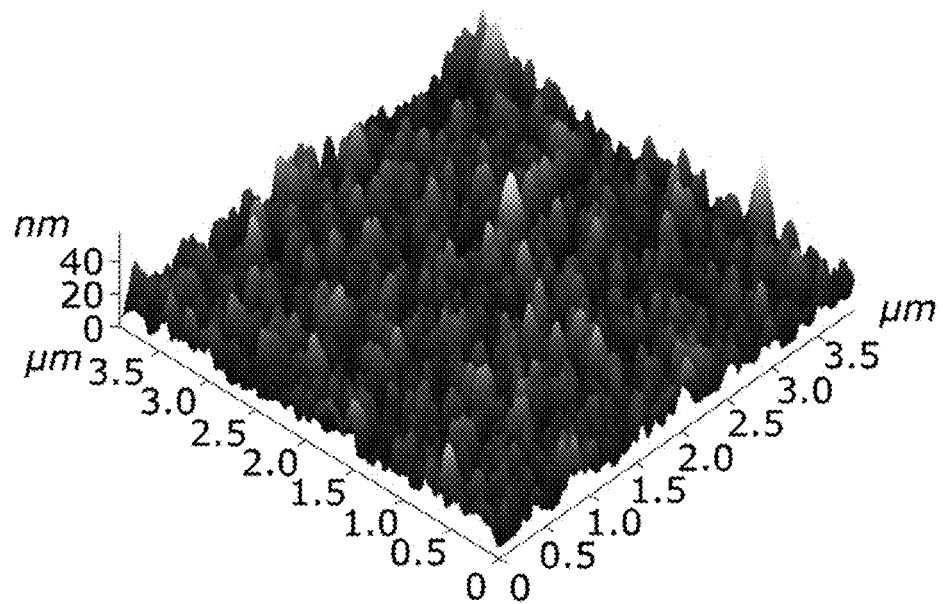
FIG. 2 shows representative atomic force microscopy (AFM) image showing the particles with vertical dimensions ranging from approx. 20 to 40 nm prepared according to Example 1.
Figure 3:
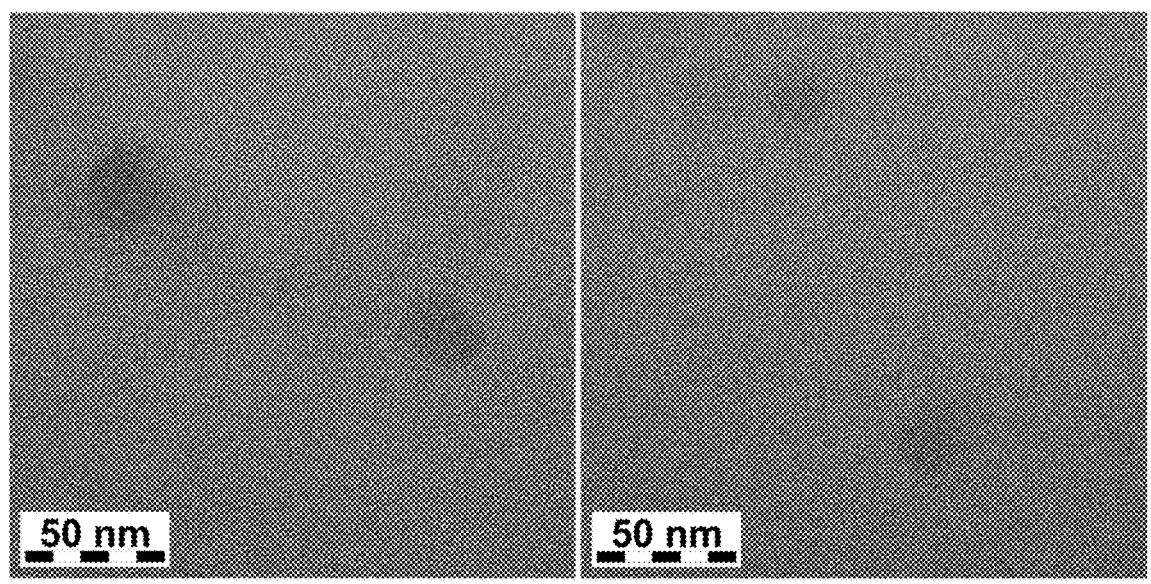
FIG. 3 shows representative transmission electron microscopy (TEM) images of the nanoparticles (approx. 30 nm); no indication of crystal planes, no electron diffraction, overall character of a molecular assembly (nanoparticles) prepared according to Example 1.
Figure 4:
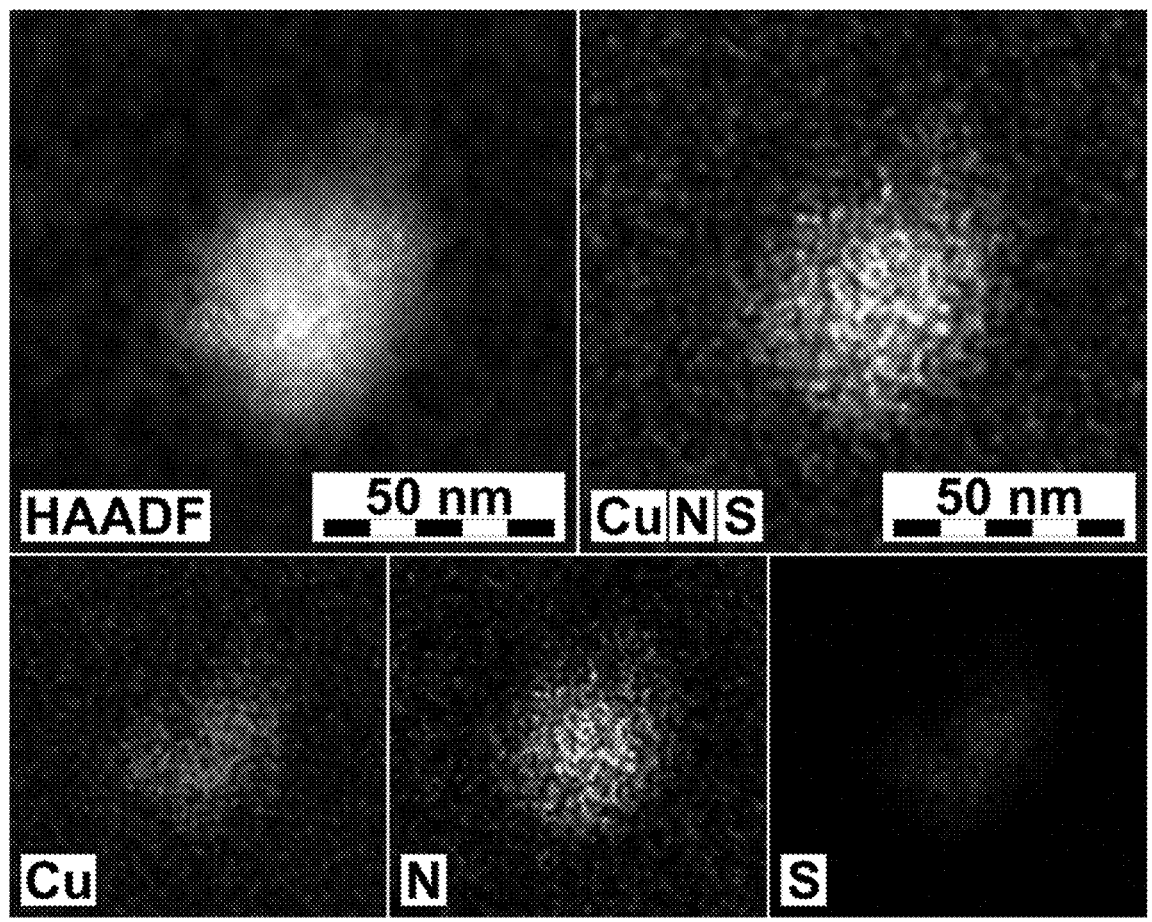
FIG. 4 shows HAADF/EDS images of cca 60 nm molecular assembly; key elements (Cu, N, S) are clearly embedded in the nano-assembly prepared according to Example 1.

Results:

The resulting solution contains 2.8 mM (1 mg/ml) of diethyldithiocarbamate-copper-HSA nanoparticles. The nanoparticles resulting from this reaction were further analysed by various advanced analytical tools including DLS, AFM, TEM, EDS and EPR depicting their basic physical and chemical properties (see FIGS. 1-5). The analyses show that the nanoparticles form a polydispersed system. The size of the particles spanned the range ca 20-100 nm with largest fraction of 20-40 nm as proved by DLS analysis (FIG. 1). AFM image (FIG. 2) and TEM image (FIG. 3) confirm the results of DLS size distribution. Moreover, transmission electron microscopy images of the nanoparticles show no indications of crystal planes (and no electron diffraction with amorphous-like pattern)—the facts confirming that nanoparticles have a character of a molecular assembly. EDS chemical mapping of single nanoparticle (FIG. 4) shows that the key elements (Cu, N, S) of copper bis(diethyldithiocarbamate) structure are homogeneously distributed within the molecular assembly. Comparative analysis by X-band EPR spectroscopy (FIG. 5) shows nearly the same spectra of the CuET embedded in the nanoparticles as the neat bis(diethyldithiocarbamate) copper complex (CuET). The estimated $g_{avg}$-values and the overall resonance profiles clearly indicate that upon encapsulation of the drug no modification of the copper oxidation and spin states (CuII, S=1/2), and no substantial alteration of the Cu octahedral-field occur. Resulting particles show also low zeta potential ($\zeta$) −35.6 mV measured by electrochemical impedance spectroscopy pointing at good stability in solution.

Figure 11:
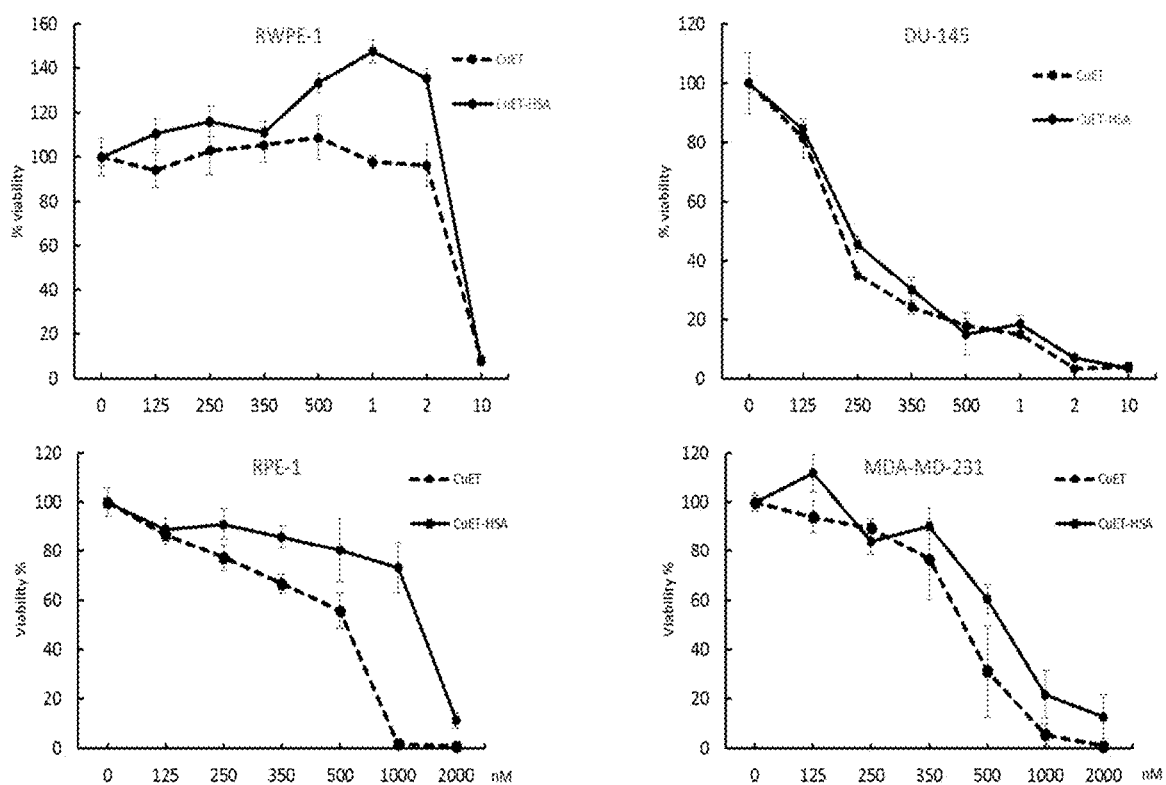
FIG. 11 shows 2,3-bis-(2-methoxy-4-nitro-5-sulfophenyl)-2H-tetrazolium-5-carboxanilide (XTT)-based cell viability analysis of CuET-albumin (CuET-HSA) nanoparticle toxicity prepared according to Example 1 after 24 hours treatment of various concentrations (from 125 nM to 10 μM). Cancer cell lines (DU-145, MDA-MB-231) show higher sensitivity compared to normal cells (RPE-1, RWPE-1). CuET-HSA nanoparticle has similar potency as neat CuET powder dissolved in dimethyl sulfoxide (DMSO) in cancer cell lines, but it is more tolerated by normal cells.

The dispersion of nanoparticles was also tested in biological experiments involving cytotoxicity tests on a panel of human cell lines derived from cancers including plasmacytoma (AMO-1; LD50=63 nM), pancreatic adenocarcinoma (Capan-1; LD50=64 nM), multiple myeloma (MM1s; LD50=69 nM), acute lymphoblastic leukemia (CCRF-CEM; LD50=70 nM), ovarian adenocarcinoma (OVCAR3; LD50=83 nM), lung carcinoma (A549; LD50=91 nM), colorectal carcinoma (HCT116; LD50=117 nM), salivary gland carcinoma (A253; LD50=214 nM), renal cell adenocarcinoma (786-0; LD50=235 nM), osteosarcoma (U20S; LD50=271 nM), squamous cell carcinoma (FADU; LD50=330 nM, SiHA; LD50=777 nM), chronic myelogenous leukemia (K562; LD50=318 nM), breast adenocarcinoma (MDA-MB-231; LD50=517 nM), glioblastoma (U87-MG; LD50=696 nM), and primary (normal) cells including normal retinal epithelial cells (hTERT-PRE1; LD50=>1000 nM) and normal prostate epithelial cells (RWPE; LD50>2000 nM). Toxicity of the nanoparticles was tested in the XTT-based cell viability assay. Cancer cell lines (DU-145, MDA-MB-231) show higher sensitivity compared to normal cells (RPE-1, RWPE-1). Importantly, CuET-HSA nanoparticle has similar potency as neat CuET powder dissolved in dimethyl sulfoxide (DMSO) in cancer cell lines, but it is more tolerated by normal cells suggesting general preferential toxicity to tumour cells (see FIG. 11).

The dispersion of nanoparticles was also examined in a long-term storage stability test at 4° C. As readout the activity in cell culture was chosen. Nanoparticles stored for 4 weeks at 4° C. showed similar potency in terms of cellular toxicity as freshly prepared nanoparticles in the XTT cell viability test using osteosarcoma line U20S (LD50 280 nM compared to 271 nM).

The dispersion of nanoparticles was also tested for the possibility of drying and follow-up re-solubilisation. The nanoparticles were dried under vacuum for 16 hours at room temperature. Dried powder was stored at 4° C. for one week and then mixed with sterile water and keep on shaker for 24 hours to achieve complete re-solubilisation. Resulting re-solubilized nanoparticles were analysed by DLS and electrochemical impedance spectroscopy. Measured most probable average particle size of 82 nm and zeta potential (ζ)-40 mV indicates minimal changes in the chemical/physical properties of nanoparticles after drying and re-solubilisation process.

Example 2

Figure 6:
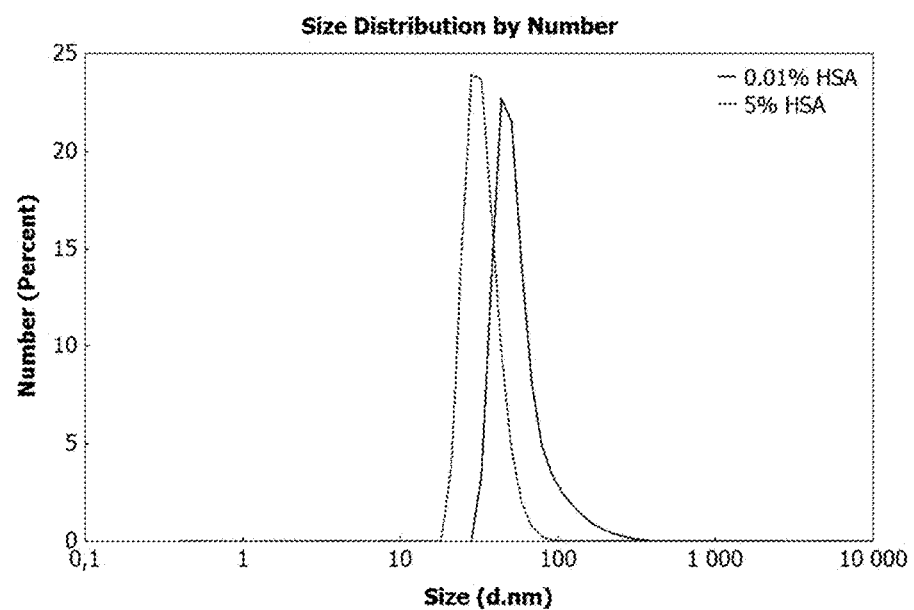
FIG. 6 shows DLS spectra (upper image) and representative TEM images (lower two images) of polydispersed system of nanoparticles formed during chemical reaction in the presence of 0.01% albumin (Example 2) or 5% albumin (Example 3). The analysis shows a prominent shift towards smaller particles in case higher albumin concentration is entering the chemical reaction.
Figure 6:
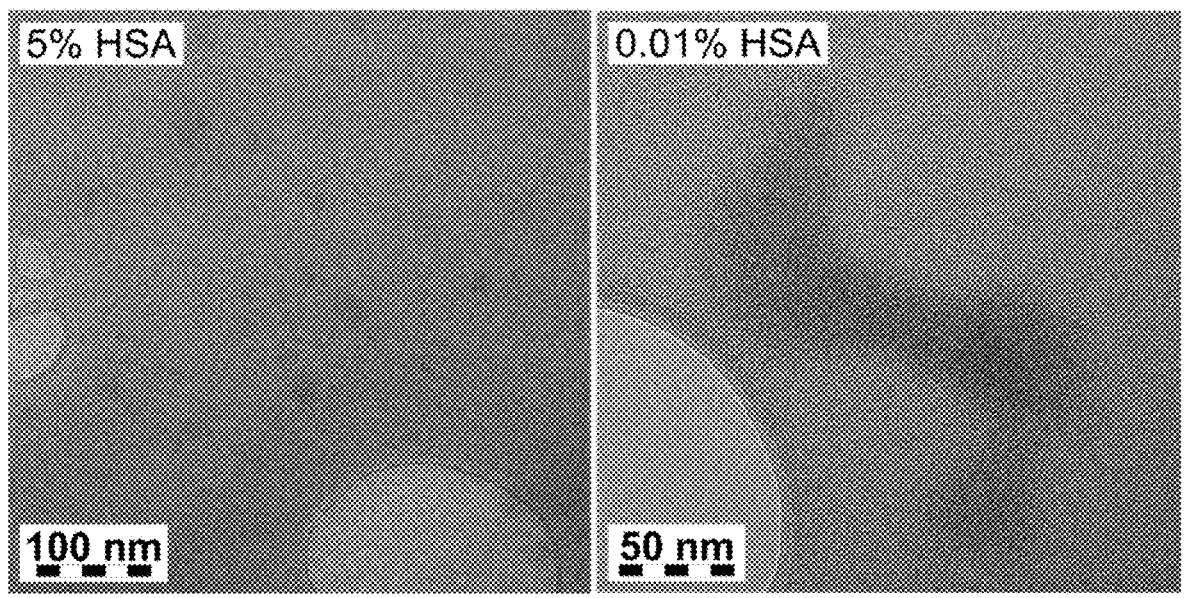

Preparation of Dispersion of Nanoparticles from 0.01% Human Serum Albumin (HSA) and Diethyldithiocarbamate and Copper Chloride Salt.
Procedure:
An injectable aqueous 20% (w/v) HSA solution in accordance with FDA specifications (pH=6.9±0.5) is diluted to 0.01% (w/v) with sterile water for injections. Sterile solution of diethyldithiocarbamate sodium salt (DTC) solubilised in water of a concentration 280 mM is added to 0.01% HSA to final concentration 5.6 mM, followed by brief stirring. To the 0.01% HSA solution containing 5.6 mM DTC is added sterile copper (ii) chloride (1M concentration in water) to final concentration 2.8 mM, followed by brief stirring.
Results
Resulting solution contains 2.8 mM (1 mg/ml) of diethyldithiocarbamate-copper-HSA nanoparticles. Then nanoparticles were further examined by DLS and TEM showing that the major fraction of nanoparticles is approx. 50-60 nm with a significant fraction of larger particles, but the sizes did not exceed 500 nm (see FIG. 6).

Example 3

Preparation of Dispersion of Nanoparticles from 5% Human Serum Albumin (HSA) and Diethyldithiocarbamate and Copper Chloride Salt.
Procedure:
An injectable aqueous 20% (w/v) HSA solution in accordance with FDA specifications (pH=6.9±0.5) is diluted to 5% (w/v) with sterile water for injections. Sterile solution of diethyldithiocarbamate sodium salt (DTC) solubilised in water of a concentration 280 mM is added to 5% HSA to final concentration 5.6 mM, followed by brief stirring. To the 5% HSA solution containing 5.6 mM DTC is added sterile copper (ii) chloride (1 M concentration in water) to final concentration 2.8 mM, followed by brief stirring.
Results
Resulting solution contains 2.8 mM (1 mg/ml) of diethyldithiocarbamate-copper-HSA nanoparticles. This reaction results into nanoparticles which were examined by DLS and TEM showing the major fraction of particles approx. 20-30 nm; generally the size distribution is significantly shifted towards smaller particles with increased HSA concentration (See FIG. 6).

Example 4

Figure 7:
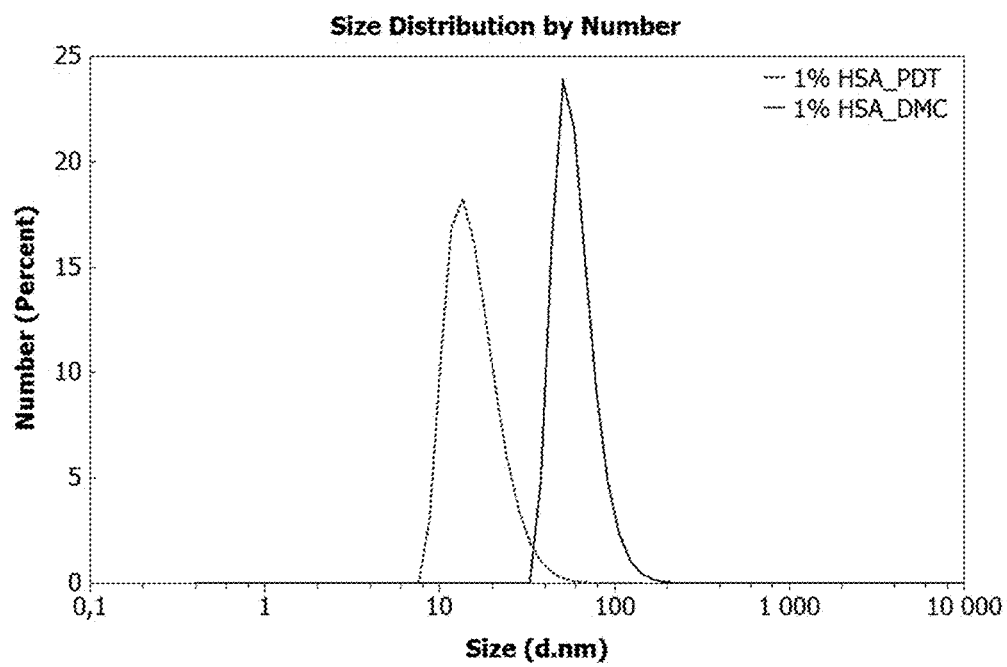
FIG. 7 shows DLS size distribution (upper image) and representative TEM images (lower two images) of the formed nanoparticles depicting different size of formed nanoparticles (Examples 4, 5) depending on the used type of dithiocarbamate (dimethylditihiocarbamate—DMC vs pyrrolidinedithiocarbamate—PDT).
Figure 7:
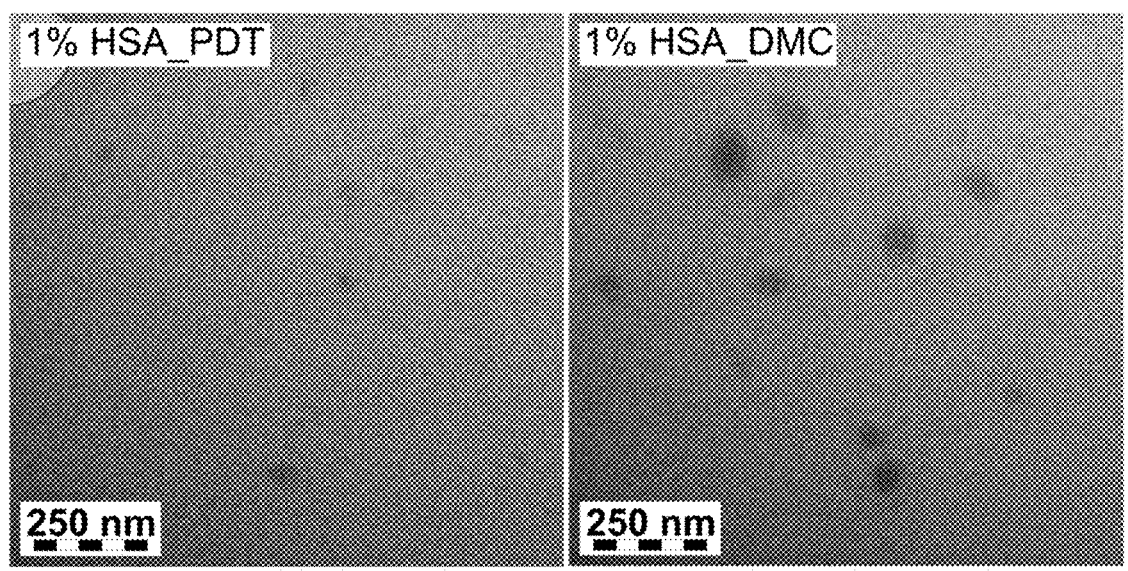

Preparation of Dispersion of Nanoparticles from 1% Human Serum Albumin (HSA) and Dimethyldithiocarbamate and Copper Chloride Salt.
Procedure:
An injectable aqueous 20% (w/v) HSA solution in accordance with FDA specifications (pH=6.9±0.5) is diluted to 1% (w/v) with sterile water for injections. Sterile solution of dimethyldithiocarbamate sodium salt (DMC) solubilised in water of a concentration 280 mM is added to 1% HSA to final concentration 5.6 mM, followed by brief stirring. To the 1% HSA solution containing 5.6 mM DMC is added sterile copper (ii) chloride (1 M concentration in water) to final concentration 2.8 mM, followed by brief stirring.
Results
Resulting solution contains 2.8 mM (1 mg/ml) of dimethyldithiocarbamate-copper-HSA nanoparticles. This reaction results into nanoparticles which were examined by DLS and TEM showing a major fraction of particles in the range of 60-70 nm (see FIG. 7.).

Example 5

Preparation of Dispersion of Nanoparticles from 1% Human Serum Albumin (HSA) and Pyrrolidinedithiocarbamate and Copper Chloride Salt.
Procedure:
An injectable aqueous 20% (w/v) HSA solution in accordance with FDA specifications (pH=6.9±0.5) is diluted to 1% (w/v) with sterile water for injections. Sterile solution of pyrrolidinedithiocarbamate ammonium salt (PDC) solubilised in water of a concentration 280 mM is added to 1% HSA to final concentration 5.6 mM, followed by brief stirring. To the 1% HSA solution containing 5.6 mM PDC is added sterile copper (ii) chloride (1 M concentration in water) to final concentration 2.8 mM, followed by brief stirring.
Results
Resulting solution contains 2.8 mM (1 mg/ml) of pyrrolidinedithiocarbamate-copper-HSA nanoparticles. This reaction results into nanoparticles which were examined by DLS and TEM showing a major fraction of particles about 15 nm (see FIG. 7). Evidently, dimethylditihiocarbamate with albumin forms larger particles compared to pyrrolidinedithiocarbamate (PDT) with albumin despite all the other conditions of the two reactions being identical. This fact reflects that smaller particles are formed with longer R1, R2 groups.

Example 6

Preparation of Dispersion of Nanoparticles from 1% Human Serum Transferrin and Diethyldithiocarbamate and Copper Chloride Salt.
Procedure:
An injectable aqueous 1% (w/v) human serum transferrin solution is prepared in sterile water for injections. Sterile solution of diethyldithiocarbamate sodium salt (DTC) solubilised in water of a concentration 280 mM is added to 1% transferrin to final concentration 5.6 mM, followed by brief stirring. To the 1% transferrin solution containing 5.6 mM DTC is added sterile copper (ii) chloride (1 M concentration in water) to final concentration 2.8 mM, followed by brief stirring.
Results
Resulting solution contain 2.8 mM (1 mg/ml) of diethyldithiocarbamate-copper-transferrin nanoparticles. This reaction results into nanoparticles which were examined by DLS showing most probable average size of approx. 60 nm. Resulting particles show low zeta potential (ζ) −21.5 mV measured by electrochemical impedance spectroscopy pointing at good stability in solution.

Example 7

Figure 8:
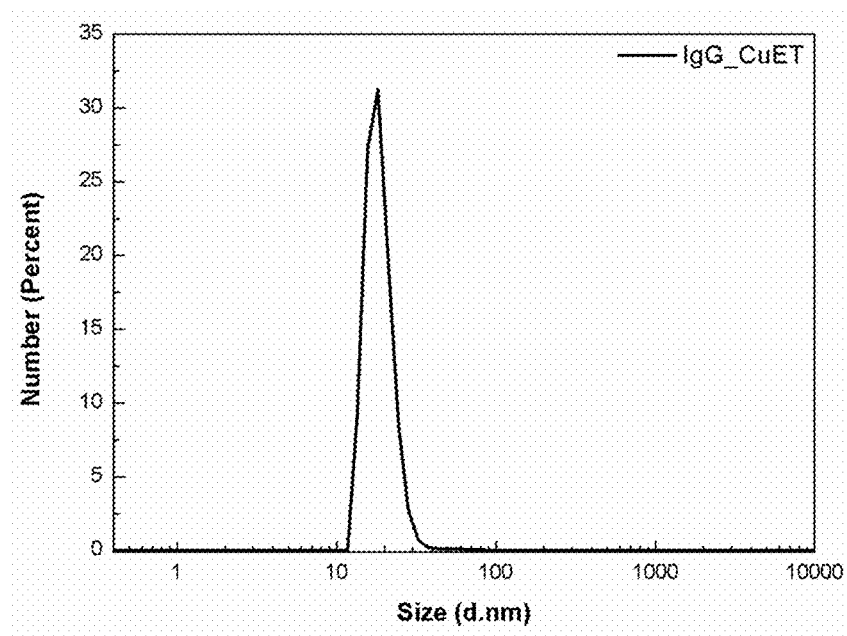
FIG. 8 shows dynamic light scattering (DLS) spectra of the nanoparticles prepared in Example 7. The nanoparticles form a polydispersed system: ca 10-40 nm; largest fraction: 15-30 nm.

Preparation of Dispersion of Nanoparticles from 1% Human Serum Immunoglobulin (IgG) and Diethyldithiocarbamate and Copper Chloride Salt.
Procedure:

An injectable aqueous 1% (w/v) immunoglobulin solution (human gamma-globulin fraction) is prepared in sterile water for injections. Sterile solution of diethyldithiocarbamate sodium salt (DTC) solubilised in water of a concentration 280 mM is added to 1% transferrin to final concentration 5.6 mM, followed by brief stirring. To the 1% immunoglobulin solution containing 5.6 mM DTC is added sterile copper (ii) chloride (1 M concentration in water) to final concentration 2.8 mM, followed by brief stirring.
Results Resulting solution contain nearly 2.8 mM (1 mg/ml) of diethyldithiocarbamate-copper-immunoglobulin nanoparticles. This reaction results into nanoparticles which were examined by DLS showing most probable average size of approx. 20 nm (see FIG. 8). Resulting particles show zeta potential (ζ) −1.39 mV as measured by electrochemical impedance spectroscopy pointing at relatively poor stability in solution.

Example 8

Figure 9:
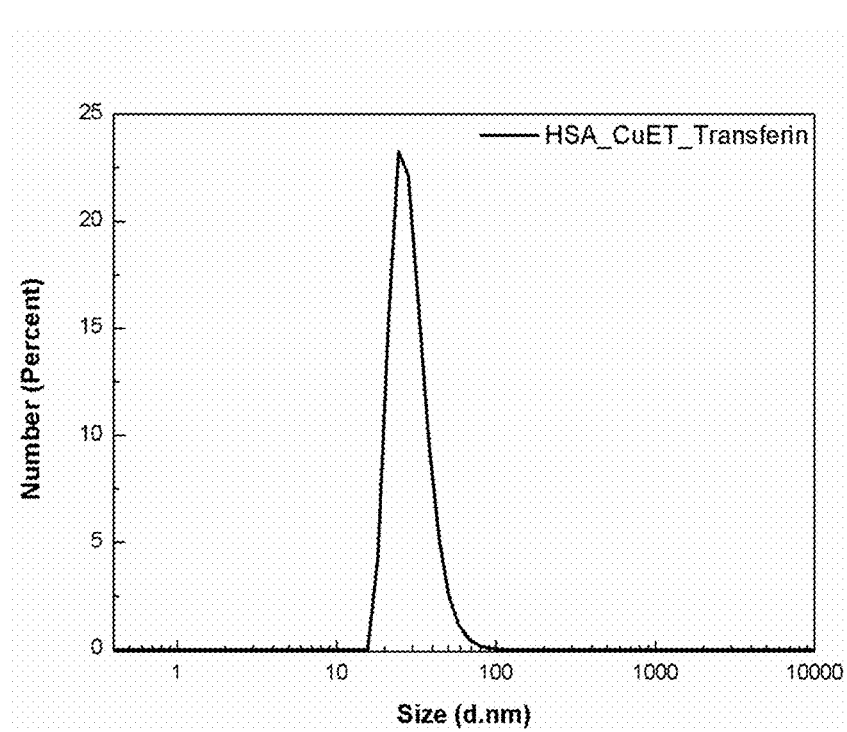
FIG. 9 shows dynamic light scattering (DLS) spectra of the nanoparticles prepared in Example 8. The nanoparticles form a polydispersed system: ca 15-100 nm; largest fraction: 20-40 nm.

Preparation of Dispersion of Nanoparticles from a Mixture of 1% Human Serum Transferrin and 1% Human Serum Albumin and Diethyldithiocarbamate and Copper Chloride Salt.
Procedure:

An injectable aqueous 1% (w/v) human serum transferrin solution is mixed with an injectable aqueous 1% (w/v) HSA solution. Sterile solution of diethyldithiocarbamate sodium salt (DTC) solubilised in water of a concentration 280 mM is added to the mixture of proteins to final concentration 5.6 mM, followed by brief stirring. To the protein solution containing 5.6 mM DTC is added sterile copper (ii) chloride (1 M concentration in water) to final concentration 2.8 mM, followed by brief stirring.
Results Resulting solution contain 2.8 mM (1 mg/ml) of diethyldithiocarbamate-copper-transferrin/HSA nanoparticles. This reaction results into nanoparticles which were examined by DLS showing most probable average size of approx. 30 nm (see FIG. 9).

Example 9

Preparation of Dispersion of Nanoparticles from a Mixture of 1% Human Serum Albumin and 1% (w/v) Immunoglobulin Solution and Diethyldithiocarbamate and Copper Chloride Salt.

Experimental Setup

Figure 10:
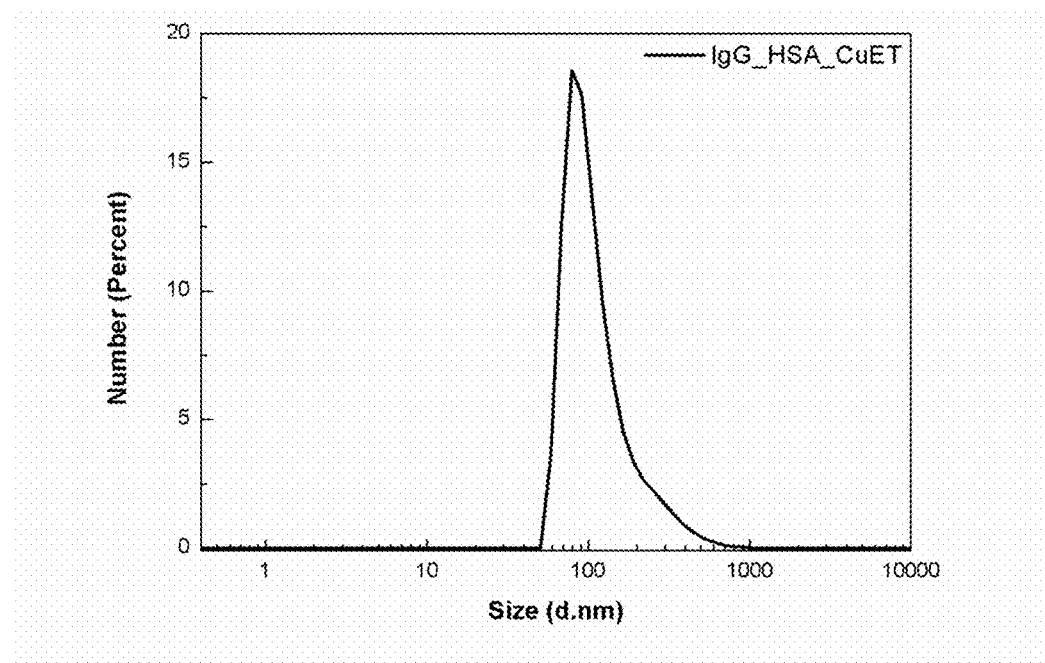
FIG. 10 shows dynamic light scattering (DLS) spectra of the nanoparticles prepared in Example 9. The nanoparticles form a polydispersed system: ca 50-800 nm; largest fraction: 60-200 nm.

An injectable aqueous 1% (w/v) human serum albumin solution is mixed with an injectable aqueous 1% (w/v) immunoglobulin solution. Sterile solution of diethyldithiocarbamate sodium salt (DTC) solubilised in water of a concentration 280 mM is added to the mixture of proteins to final concentration 5.6 mM, followed by brief stirring. To the protein solution containing 5.6 mM DTC is added sterile copper (ii) chloride (1 M concentration in water) to final concentration 2.8 mM, followed by brief stirring.
Results Resulting solution contains 2.8 mM (1 mg/ml) of diethyldithiocarbamate-copper-albumin/immunoglobulin nanoparticles. This reaction results into nanoparticles which were examined by DLS showing most probable average size of approx. 120 nm (see FIG. 10).

Example 10

Preparation of Dispersion of Nanoparticles from 0.2% Mouse Serum Albumin (MSA) and Diethyldithiocarbamate and Radioactive Copper ($^{64}$Cu) Acetate Salt for Tumour Imaging and Biodistribution.

Experimental Setup

Figure 13:
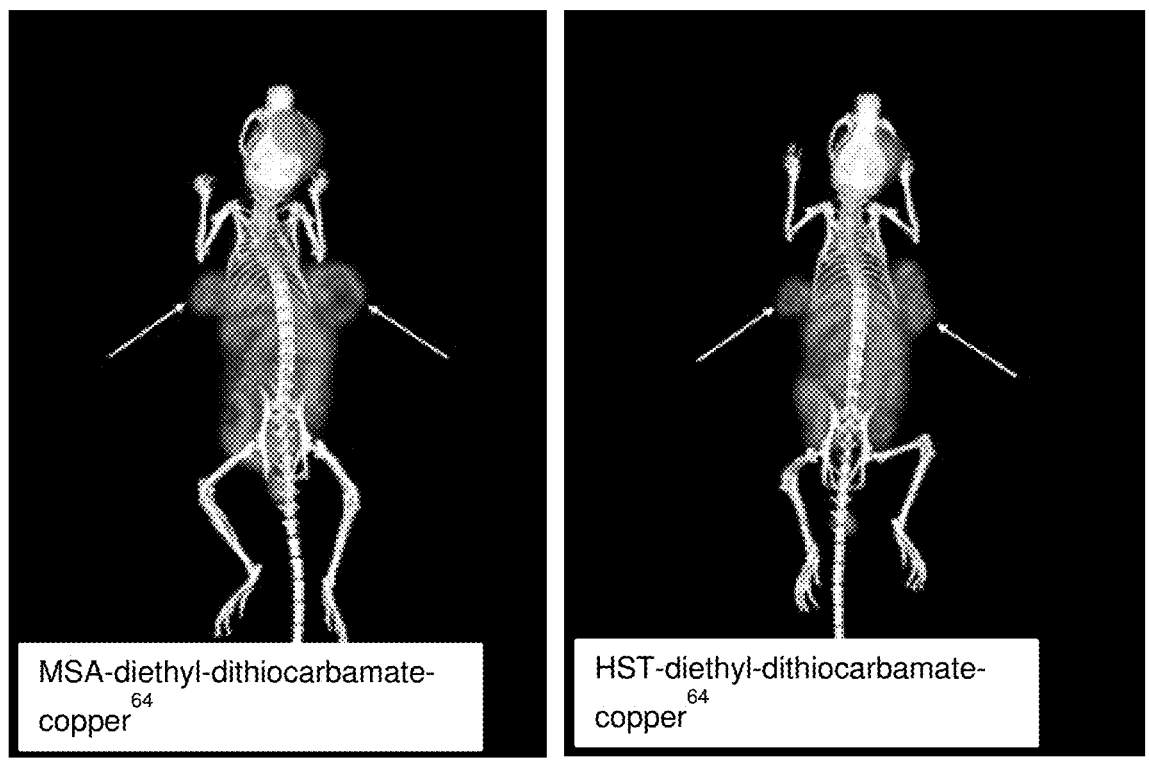
FIG. 13 shows the presence of the $^{64}$Cu radioisotope in the tumours (marked by arrows) visualised by combined positron emission tomography combined with computer tomography (PET/CT) imaging in severe combined immunodeficiency (SCID) mouse. The PET signal was collected 22 hours after the retro-orbital injection of dispersion of nanoparticles of MSA-diethyl-dithiocarbamate-copper$^{64}$ nanoparticles (left) and dispersion of nanoparticles of human transferrin-diethyl-dithiocarbamate-copper$^{64}$ nanoparticles (right) prepared according to examples 10 and 11 respectively. PET signal shows that the $^{64}$Cu embedded in complexes is accumulated within the MDA-MB-231 subcutaneous tumour mass. GIT positivity indicates that the compounds are excreted by intestinal tract.

Sterile solution of diethyldithiocarbamate sodium salt (DTC) solubilised in water of a concentration 280 mM is added to 1% MSA to final concentration 5.6 mM, followed by brief stirring. To the 1% MSA solution containing 5.6 mM DTC is added a mixture of sterile copper ($^{64}$Cu) (ii) acetate and non-active copper chloride (100 mM concentration in water) to final concentration 2.8 mM, followed by brief stirring.
Results Resulting solution contains 2.8 mM (1 mg/ml) of diethyldithiocarbamate-copper ($^{64}$Cu)-MSA nanoparticles. The nanoparticles resulting from this reaction were further applied in-vivo by retro-orbital injection (dose 1 mg/kg corresponding to activity 33 MBq) into mice bearing subcutaneous MDA-MB-231 tumour xenograft followed by the PET analysis in multiple time points after the application using Albira PET/SPECT/CT imaging system (Bruker Biospin Corporation, Woodbridge, Conn., USA). Measured PET signal shows accumulation within the tumour mass (FIG. 13).

Example 11

Preparation of Dispersion of Nanoparticles from 0.2% Human Serum Transferin (HST) and Diethyldithiocarbamate and Radioactive Copper ($^{64}$Cu) Acetate Salt for Tumour Imaging and Biodistribution.

Experimental Setup

Sterile solution of diethyldithiocarbamate sodium salt (DTC) solubilised in water of a concentration 280 mM is added to 1% HST to final concentration 5.6 mM, followed by brief stirring. To the 1% HST solution containing 5.6 mM DTC is added a mixture of sterile copper ($^{64}$Cu) (ii) acetate and non-active copper chloride (100 mM concentration in water) to final concentration 2.8 mM, followed by brief stirring.
Results Resulting solution contains 2.8 mM (1 mg/ml) of diethyldithiocarbamate-copper ($^{64}$Cu)-HST nanoparticles. The nanoparticles resulting from this reaction were further applied in-vivo by retro-orbital injection (dose 1 mg/kg corresponding to activity 29 MBq) into mice bearing subcutaneous MDA-MB-231 tumour xenograft followed by the PET analysis in multiple time points after the application using Albira PET/SPECT/CT imaging system (Bruker Biospin Corporation, Woodbridge, Conn., USA). PET signal shows accumulation within the tumour mass (FIG. 13).

Example 12

Preparation of Dispersion of Nanoparticles from 0.2% Mouse Serum Albumin (MSA) and Diethyldithiocarbamate and Copper Chloride Salt.

Experimental Setup

An injectable aqueous 20% (w/v) MSA solution (pH=6.9±0.5) is diluted to 0.2% (w/v) with sterile water for injections. Sterile solution of diethyldithiocarbamate sodium salt (DTC) solubilised in water of a concentration 280 mM is added to 0.2% MSA to final concentration 5.6 mM, followed by brief stirring. To the 0.2% MSA solution containing 5.6 mM DTC is added sterile copper (ii) chloride (1 M concentration in water) to final concentration 2.8 mM, followed by brief stirring.

Results

Figure 12:
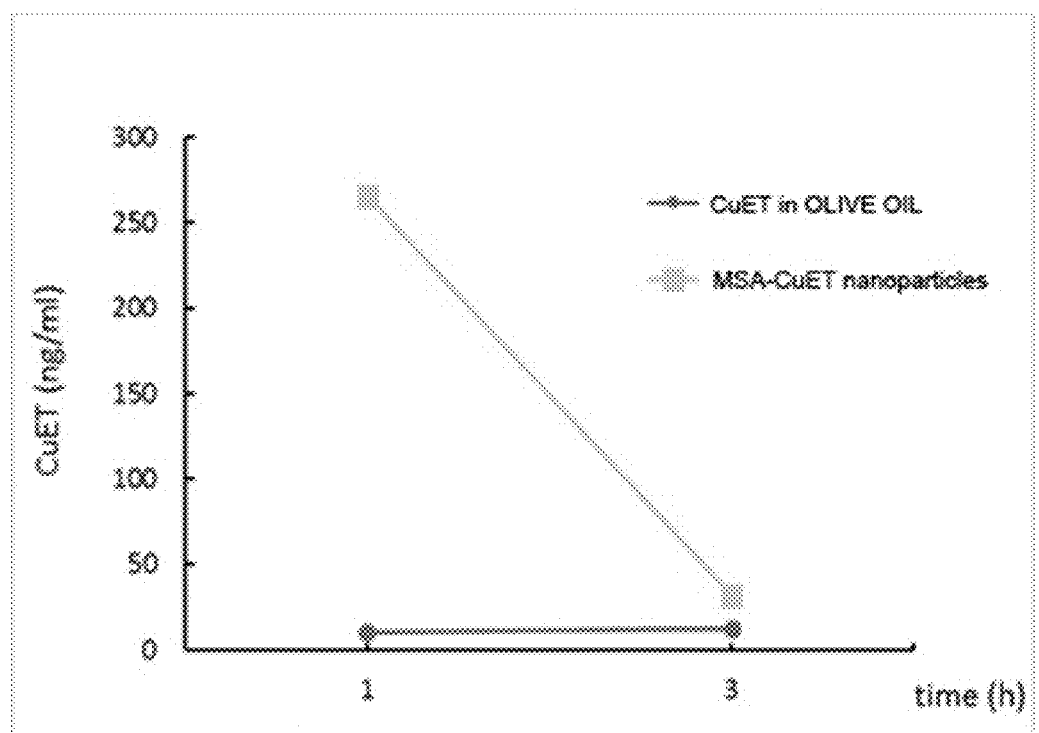
FIG. 12 shows high pressure liquid chromatography coupled to time-of-flight mass spectrometry (HPLC-TOF/MS) analysis of CuET concentrations in mice serum after single i.p. application of 5 mg/kg CuET formulated as albumin nanoparticle according to Example 1 or as the neat CuET powder (obtained from TOKYO CHEMICAL INDUSTRY CO., LTD.) dissolved in olive oil which is a standard formulation for non-polar compounds applied intraperitoneally in the mice experiments. Measured concentrations show significantly higher circulating concentrations of CuET in case of the nanoparticle formulation.
Figure 14:
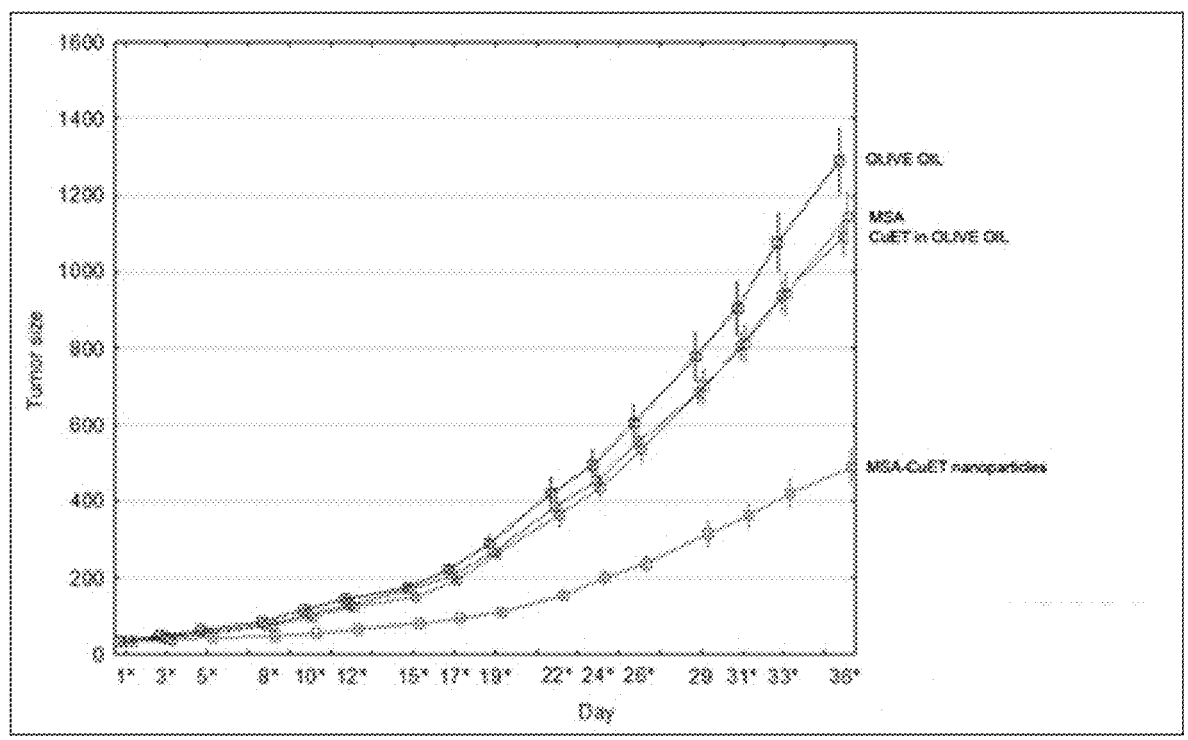
FIG. 14 shows the growth of MDA-MB-231 breast cancer tumours subcutaneously xenografted into the SCID mice after treatment with CuET (1 mg/ml) formulated as either albumin nanoparticle according to Example 1 or as the neat CuET powder (obtained from TOKYO CHEMICAL INDUSTRY CO., LTD.) dissolved in olive oil which is a standard formulation for non-polar compounds applied intraperitoneally in the mice experiments. Only the CuET-albumin nanoparticle shows significant effect on the tumour growth.
Figure 15:
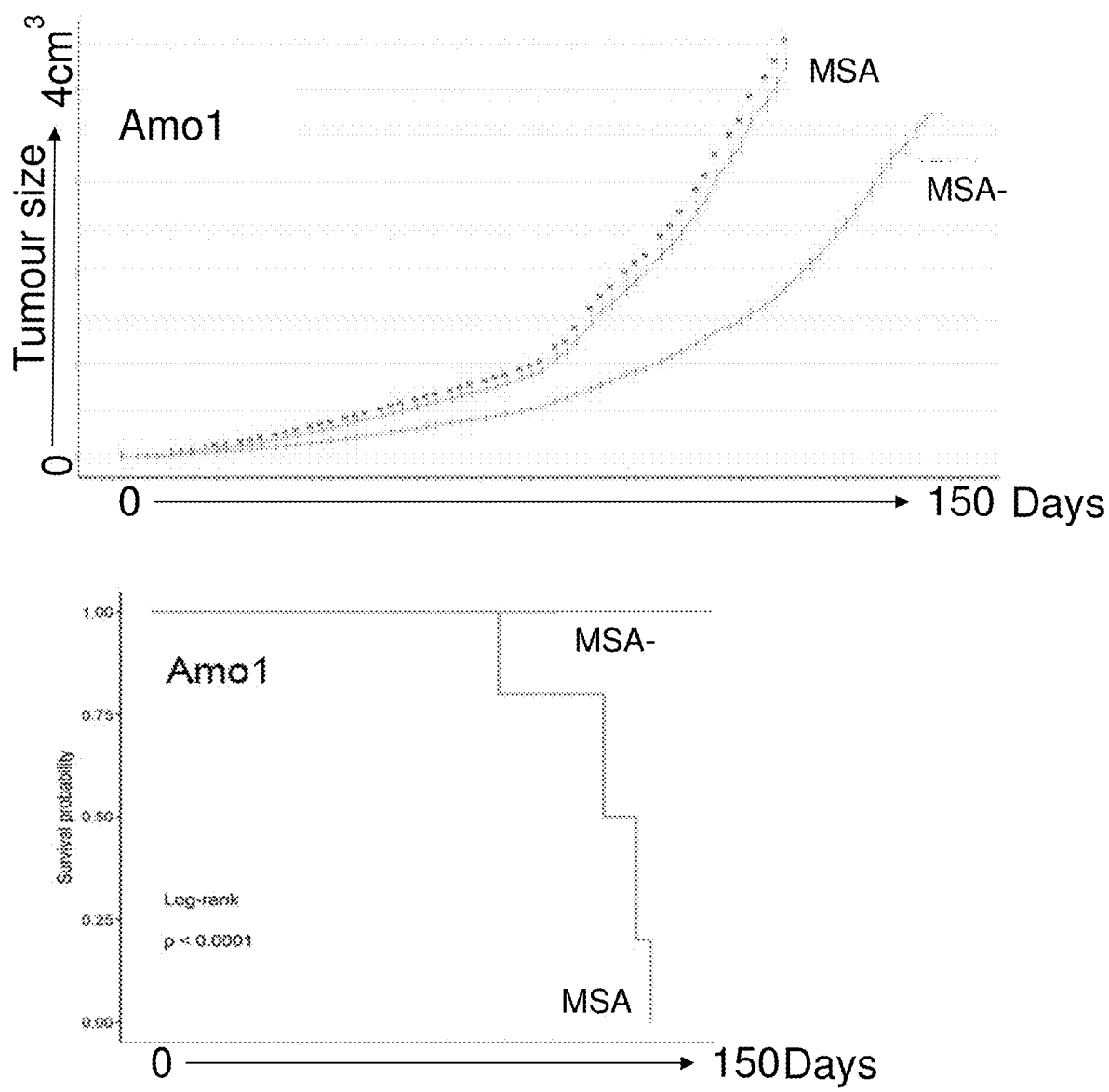
FIG. 15 shows the growth of AMO-1 tumours subcutaneously xenografted into the SCID mice treated with CuET (1 mg/ml) formulated as albumin nanoparticle according to Example 1. The nanoparticles treatment significantly reduces the tumour growth (upper image, callipers) and the treated animals show prolonged survival (lower image, Kaplan-Meyer survival plots) compared to control mice treated only by albumin. The animals were treated by intraperitoneal application once a day in a regime 5 days' treatment+2 days off. These experiments points also at a very good tolerability of the CuET-albumin nanoparticles as the animals were injected more than 100 times.

Resulting solution contains 2.8 mM (1 mg/ml) of diethyldithiocarbamate-copper-MSA nanoparticles. The nanoparticles resulting from this reaction were further analysed by various mouse in-vivo experiments including serum pharmacokinetics of CuET by HPLC/MS (see FIG. 12). Animals were treated intraperitoneally by nanoparticles in concentration corresponding to 5 mg/kg of CuET. Serum was collected at 1 and 3 hours after administration. As control 5 mg/kg of CuET dispersed in olive oil was used. For antitumor activity the nanoparticles were administered in concentration corresponding to 1 mg/kg of CuET (see FIGS. 14-15 and methods). CuET concentration was also analysed by HPLC/MS in brain tissue (see methods). Animals were treated intraperitoneally by nanoparticles in concentration corresponding to 1 mg/kg of CuET. 1 hour after intraperitoneal administration the brain CuET levels were similar to blood levels and reached approximately 3 ng/ml. This indicates very good penetration of CuET formulated as MSA nanoparticles through blood-brain barrier.

Example 13

Preparation of Dispersion of Nanoparticles from 0.2% Human Serum Albumin (HSA) and Copper Chloride Salt and Diethyldithiocarbamate.

Experimental Setup

An injectable aqueous 20% (w/v) MSA solution (pH=6.9±0.5) is diluted to 0.2% (w/v) with sterile water for injections. Sterile solution of sterile copper (ii) chloride solubilised in water of a concentration 1 M is added to 0.2% HSA to final concentration 2.8 mM, followed by brief stirring. To the 0.2% HSA solution containing 2.8 mM copper (ii) chloride is added sterile diethyldithiocarbamate sodium salt (280 mM concentration in water) to final concentration 5.6 mM, followed by brief stirring.

Results

Resulting solution contains 2.8 mM (1 mg/ml) of diethyldithiocarbamate-copper-HSA nanoparticles.

Example 14

Proteomic Identification of Plasmatic Proteins Capable of Forming Nanoparticles with Copper Chloride Salt and Diethyldithiocarbamate Experimental Setup Heparin plasma from healthy volunteer is pre-cleaned by ultracentrifugation (200000 g for 3 hours at 4° C.) to remove all precipitates and large complexes naturally occurring in plasma. Sterile solution of diethyldithiocarbamate sodium salt (DTC) solubilised in water of a concentration 280 mM is added to pre-cleaned plasma to final concentration 5.6 mM, followed by brief stirring. To the pre-cleaned plasma containing 5.6 mM DTC is added sterile copper (ii) chloride (1 M concentration in water) to final concentration 2.8 mM, followed by brief stirring. Nanoparticle solution is filtered by 450 nm pore filter (Millipore) to remove all large particles. Filtered solution is ultracentrifuged (200000 g for 3 hours at 4° C.) to isolate nanoparticles. Pellet containing nanoparticles is washed and resuspended in physiological saline to remove potential contaminants and again ultracentrifuged (200000 g for 3 hours at 4° C.). Pellet containing nanoparticles is solubilised in 80% acetone to precipitate and isolate proteins. Proteins are further used for HPLC-MS based proteomic identification (the identified proteins show that many blood proteins are capable of forming nanoparticulate forms of the present invention).

Results

Resulting solution contains 2.8 mM (1 mg/ml) of diethyldithiocarbamate-copper nanoparticles with various plasmatic proteins that were further identified by HPLC-MS proteomics. Following proteins were identified: Fibrinogen beta chain; Fibrinogen gamma chain; Alpha-2-macroglobulin; Fibrinogen alpha chain; Ig mu chain C region; Apolipoprotein A-I; Apolipoprotein C-III; Ig mu heavy chain disease protein; Ig kappa chain C region; Serum albumin; CD5 antigen-like; Clusterin; Ig gamma-1 chain C region; Apolipoprotein B-100; Apolipoprotein B-48; Apolipoprotein A-IV; Ig alpha-1 chain C region; Fibronectin; Anastellin; Ugl-Y1; Ugl-Y2; Ugl-Y3; Immunoglobulin lambda-like polypeptide 5; Ig lambda-1 chain C regions; C4b-binding protein alpha chain; Apolipoprotein C-I; Truncated apolipoprotein C-I; Complement C3; Complement C3 beta chain; C3-beta-c; Complement C3 alpha chain; C3a anaphylatoxin; Acylation stimulating protein; Complement C3b alpha chain; Complement C3c alpha chain fragment 1; Complement C3dg fragment; Complement C3 g fragment; Complement C3d fragment; Complement C3f fragment; Complement C3c alpha chain fragment 2; Uncharacterized protein C1orf177; Complement C1r subcomponent; Complement C1r subcomponent heavy chain; Complement C1r subcomponent light chain; Complement C1s subcomponent; Complement C1s subcomponent heavy chain; Complement C1s subcomponent light chain; Inter-alpha-trypsin inhibitor heavy chain H4; 70 kDa inter-alpha-trypsin inhibitor heavy chain H4; 35 kDa inter-alpha-trypsin inhibitor heavy chain H4; Vitronectin; Vitronectin V65 subunit; Vitronectin V10 subunit; Somatomedin-B; Apolipoprotein C-II; Proapolipoprotein C-II; Complement C1q subcomponent subunit B; Immunoglobulin J chain; Complement factor H; Apolipoprotein A-II; Proapolipoprotein A-II; Truncated apolipoprotein A-II; Ig gamma-3 chain C region; Ig gamma-4 chain C region; Complement C1q subcomponent subunit A; Haptoglobin-related protein; Apolipoprotein E; Haptoglobin; Haptoglobin alpha chain; Haptoglobin beta chain; Complement C4-A; Complement C4 beta chain; Complement C4-A alpha chain; C4a anaphylatoxin; C4b-A; C4d-A; Complement C4 gamma chain; Complement C4-B; Complement C4 beta chain; Complement C4-B alpha chain; C4a anaphylatoxin; C4b-B; C4d-B; Complement C4 gamma chain; Transthyretin; Hemoglobin subunit beta; LVV-hemorphin-7; Spinorphin; Galectin-3-binding protein; Ficolin-3; Ig gamma-2 chain C region; Plasminogen; Plasmin heavy chain A; Activation peptide; Angiostatin; Plasmin heavy chain A, short form; Plasmin light chain B; Complement C1q subcomponent subunit C; Histidine-rich glycoprotein; Ig heavy chain V-III region CAM; Ig heavy chain V-III region 23; Ig kappa chain V-IV region; Ig heavy chain V-III region BUT; Ig heavy chain V-III region KOL; Ig heavy chain V-III region WEA; Ig heavy chain V-III region TRO; Ig alpha-2 chain C region; Ig lambda-3 chain C regions; Ig lambda-2 chain C regions; Ig lambda-6 chain C region; Ig lambda-7 chain C region; Ig kappa chain V-III region VG; Apolipoprotein D; Apolipoprotein(a); Gelsolin; Inter-alpha-trypsin inhibitor heavy chain H1; Prothrombin; Activation peptide fragment 1; Activation peptide fragment 2; Thrombin light chain; Thrombin heavy chain; Ceruloplasmin; Vitamin K-dependent protein S; Ig lambda chain V-I region HA; Ig lambda chain V-I region VOR; Complement C5; Complement C5 beta chain; Complement C5 alpha chain; C5a anaphylatoxin; Complement C5 alpha chain; Ig kappa chain V-III region POM; Serotransferrin; Beta-2-glycoprotein 1; Inter-alpha-trypsin inhibitor heavy chain H2; Transient receptor potential cation channel subfamily M member 6; Complement component C8 alpha chain; Hemoglobin subunit alpha; Ig kappa chain V-III region B6; Kininogen-1; Kininogen-1 heavy chain; T-kinin; Bradykinin; Lysyl-bradykinin; Kininogen-1 light chain; Low molecular weight growth-promoting factor; Ig kappa chain V-II region FR; Complement component C8 beta chain; Ig heavy chain V-II region NEWM; Ig heavy chain V-II region ARH-77; Ig heavy chain V-II region WAH; C4b-binding protein beta chain; Complement factor B; Complement factor B Ba fragment; Complement factor B Bb fragment; Alpha-1-antitrypsin; Short peptide from AAT; Complement factor H-related protein 1; Complement factor H-related protein 2; Alpha-2-HS-glycoprotein; Alpha-2-HS-glycoprotein chain A; Alpha-2-HS-glycoprotein chain B; Apolipoprotein M; Apolipoprotein L1; Ig lambda chain V-I region NEWM; Ig lambda chain V-III region LOI; Coagulation factor V; Coagulation factor V heavy chain; Coagulation factor V light chain; IgGFc-binding protein; Mannan-binding lectin serine protease 1; Mannan-binding lectin serine protease 1 heavy chain; Mannan-binding lectin serine protease 1 light chain; N-acetylmuramoyl-L-alanine amidase; Plasma kallikrein; Plasma kallikrein heavy chain; Plasma kallikrein light chain; Serum paraoxonase/arylesterase 1; Protein AMBP; Alpha-1-microglobulin; Inter-alpha-trypsin inhibitor light chain; Trypstatin; Ig lambda chain V region 4A; Hemopexin; Ficolin-2; Alpha-1-acid glycoprotein 2; Alpha-1-acid glycoprotein 1; Complement component C8 gamma chain; Fibulin-1; Extracellular matrix protein 1; Coagulation factor XII; Coagulation factor XIIa heavy chain; Beta-factor XIIa part 1; Coagulation factor XIIa light chain; Kallistatin; Mannan-binding lectin serine protease 2; Mannan-binding lectin serine protease 2 A chain; Mannan-binding lectin serine protease 2 B chain; von Willebrand factor; von Willebrand antigen 2; Heparin cofactor 2; Cholesteryl ester transfer protein; SUN domain-containing protein 3; Ig delta chain C region; Complement component C6; Phosphatidylinositol-glycan-specific phospholipase D; Apolipoprotein F; Serum amyloid A-2 protein; Serum amyloid A-1 protein; Amyloid protein A; Serum amyloid protein A(2-104); Serum amyloid protein A(3-104); Serum amyloid protein A(2-103); Serum amyloid protein A(2-102); Serum amyloid protein A(4-101); 2-hydroxyacylsphingosine 1-beta-galactosyltransferase; Vitamin D-binding protein; Angiotensinogen; Angiotensin-1; Angiotensin-2; Angiotensin-3; Angiotensin-4; Angiotensin 1-9; Angiotensin 1-7; Angiotensin 1-5; Angiotensin 1-4; Keratin, type I cytoskeletal 10; Serum amyloid A-4 protein; Ig heavy chain V-II region MCE; Keratin, type I cytoskeletal 9; Ig heavy chain V-I region HG3; Ig heavy chain V-I region EU; Polycomb protein SUZ12; Afamin; Complement component C9; Complement component C9a; Complement component C9b; Keratin, type II cytoskeletal 1; Complement component C7; Coagulation factor XI; Coagulation factor XIa heavy chain; Coagulation factor XIa light chain; Alpha-2-antiplasmin; Antithrombin-III; Matrix Gla protein; Hemoglobin subunit delta; Small ubiquitin-related modifier 2; Small ubiquitin-related modifier 3; Carboxypeptidase N catalytic chain; Putative histone-lysine N-methyltransferase PRDM6; UBA-like domain-containing protein 2; Vacuolar fusion protein MON1 homolog A; Ig kappa chain V-I region HK102; Coagulation factor XIII A chain; Polymeric immunoglobulin receptor; Secretory component; Actin, cytoplasmic 1; Actin, cytoplasmic 1, N-terminally processed; Actin, cytoplasmic 2; Actin, cytoplasmic 2, N-terminally processed; Ig heavy chain V-I region V35; Inhibin beta C chain; Apolipoprotein C-IV; Mannan-binding lectin serine protease 1; Mannan-binding lectin serine protease 1 heavy chain; Mannan-binding lectin serine protease 1 light chain; Keratin, type II cytoskeletal 2 epidermal; Retinol-binding protein 4; Plasma retinol-binding protein(1-182); Plasma retinol-binding protein(1-181); Plasma retinol-binding protein(1-179); Plasma retinol-binding protein(1-176); Plasma protease C1 inhibitor; Lumican; WD repeat-containing protein 20; Sialic acid-binding Ig-like lectin 16; Alpha-1B-glycoprotein; Vinculin; Chromodomain-helicase-DNA-binding protein 7; Uncharacterized protein C17orf102; Translocation protein SEC62; Growth arrest-specific protein 6; Beta-2-microglobulin; Beta-2-microglobulin form pI 5.3; Transgelin-2; Tetranectin; Protein S100-A9; Zinc finger protein 215; Zinc finger FYVE domain-containing protein 1; Ig kappa chain V-II region Cum; Tissue factor pathway inhibitor; Fibroblast growth factor receptor 1; Pregnancy zone protein; Selenoprotein P; Phospholipid transfer protein; Myotrophin; Zinc finger MYND domain-containing protein 11; Synaptotagmin-13; Uncharacterized protein C19orf68; E3 ubiquitin-protein ligase RNF169; LIM domain only protein 7; Sorting nexin-27. Those proteins or their combinations can be used for industrial production of CuET nanoparticles.

The invention claimed is:

1. A molecular complex comprising a particulate form of dithiocarbamate-copper complex and at least one blood protein, wherein the blood protein is selected from the group consisting of albumin, transferrin, immunoglobulin, monoclonal immunoglobulin, whole blood, blood plasma and blood serum, wherein the particulate form is free of organic solvents, wherein the molecular complex has an average particle size in the range of 2-80 nm and is obtained by a process comprising the following steps:
   (a) combining a first component selected from dithiocarbamate and copper salt with at least one blood protein in an aqueous solvent, and
   (b) subsequently adding a second component selected from dithiocarbamate and copper salt,
   wherein if the first component is dithiocarbamate, then the second component is copper salt; and if the first component is copper salt, then the second component is dithiocarbamate, and
   (c) optionally lyophilizing the resulting solution;
   wherein the dithiocarbamate has a formula (R1)(R2)N—CS$_2$—, wherein R1 and R2 are the same or different and are independently selected from the group consisting of C1—C4 alkyl and C3—C6 cycloalkyl;
wherein the molecular complex contains the molecules of the dithiocarbamate-copper complex and the at least one blood protein bound together by non-covalent binding interactions, and wherein the molecular complex is not a core-shell particle.

2. The molecular complex according to claim 1, in the form of a molecular assembly, which comprises the molecules of the dithiocarbamate-copper complex and the at least one blood protein bound together by non-covalent binding interactions in a stoichiometric ratio.

3. The molecular complex according to claim 1, wherein the copper is selected from $^{63}$Cu, $^{65}$Cu, $^{64}$Cu and mixtures thereof.

4. The molecular complex according to claim 1, wherein the dithiocarbamate is diethyldithiocarbamate.

5. The molecular complex according to claim 1, having a negative zeta-potential.

6. The molecular complex according to claim 1, which is inlyophilized or spray-dried form.

7. The molecular complex according to claim 1, which is in lyophilized form and further comprises at least one cryoprotectant selected from the group consisting of mannitol, trehalose, saccharose, albumin, lactose, dextrose, sucrose, glucose, maltose, inositol, raffinose, inulin, maltodextrin, polysaccharides, heparin, 2-hydroxypropyl-β-cyclodextrin, glycerol, inositol, sorbitol, mercaptans, polyethylene glycol, adonitol, amino acids, polyoxyethylene sorbitan fatty acid esters, polyoxyethylene-polyoxypropylene copolymer, polyoxyethylene alkyl ethers, sodium dodecyl sulfate, ascorbic acid, polyvinylpyrrolidone, and dextran.

8. The molecular complex according to claim 1, which is sterile filtered.

9. The molecular complex according to claim 1, wherein the molecular complex comprises immunoglobulin or immunoglobulin-containing blood protein mixtures as blood proteins, and further harbours antibodies or antibody fragments against tumour antigens or cell specific markers.

10. The molecular complex according to claim 1, having a zeta-potential lower than −15 mV.

11. The molecular complex according to claim 1, having a zeta-potential lower than −30 mV.

12. The molecular complex according to claim 1, which is in a dry form.

13. The molecular complex according to claim 1, wherein the blood protein is human serum albumin.

14. A process for preparation of the molecular complex according to claim 1, comprising the following steps:
(a) combining a first component selected from dithiocarbamate and copper salt with at least one blood protein in an aqueous solvent, and
(b) subsequently adding a second component selected from dithiocarbamate and copper salt,
wherein if the first component is dithiocarbamate, then the second component is copper salt; and if the first component is copper salt, then the second component is dithiocarbamate, and
(c) optionally lyophilizing the resulting solution.

15. The process according to claim 14, wherein the dithiocarbamate is diethyldithiocarbamate and the blood protein is human serum albumin.

16. The process according to claim 14, comprising the steps of:
(a) solubilizing at least one blood protein in an aqueous solvent to a concentration in the range from 0.01 % (w/v) to saturated solution or providing whole blood or blood plasma or blood serum of a patient;
(b) adding at least one dithiocarbamate dissolved in an aqueous solvent in the range from 1 uM to 100 mM;
(c) subsequently to step (b), adding a copper salt solution in an aqueous solvent, having the copper salt concentration in the range from 1 uM to 100 mM.

17. The process according to claim 16, wherein the solubilizing step (a) is solubilizing at least one blood protein in an aqueous solvent to a concentration in the range from 0.1 % to 10 % (w/v), or providing whole blood or blood plasma or blood serum of a patient.

18. The process according to claim 16, wherein the adding at least one dithiocarbamate step (b) is adding at least one dithiocarbamate dissolved in an aqueous solvent in the range from 1 to 10 mM.

19. The process according to claim 16, wherein the adding a copper salt solution step (c) is adding a copper salt solution in an aqueous solvent, having the copper salt concentration in the range from 1 to 10 mM.

20. The process according to claim 16, wherein the at least one blood protein is solubilized in an aqueous solvent selected from the group consisting of water and a water-based buffer.

21. The process according to claim 14, comprising the steps of:
(a) solubilizing at least one blood protein in an aqueous solvent to a concentration in the range from 0.01% (w/v) to saturated solution or providing whole blood or blood plasma or blood serum of a patient;
(b) subsequently to step (a), adding a copper salt solution in an aqueous solvent, having the copper salt concentration in the range from 1 uM to 100 M;
(c) subsequently to step (b), adding at least one dithiocarbamate dissolved in an aqueous solvent in the dithiocarbamate in the range from 1 uM to 100 mM.

22. The process according to claim 21, wherein the solubilizing step (a) is solubilizing at least one blood protein in an aqueous solvent to a concentration in the range from 0.1 % to 10 % (w/v), or providing whole blood or blood plasma or blood serum of a patient.

23. The process according to claim 21, wherein the adding copper salt solution (b) is adding a copper salt solution in an aqueous solvent, having the copper salt concentration in the range from 1 to 10 mM.

24. The process according to claim 21, wherein the adding at least one dithiocarbamate step (c) is adding at least one dithiocarbamate dissolved in an aqueous solvent in the range from 1 to 10 mM.

25. The process according to claim 14, wherein in step (a), albumin, transferrin, immunoglobulin, or mixtures thereof, or whole blood, blood serum or blood plasma are used as blood proteins.

26. The process according to claim 14, wherein molar ratio of copper ions:dithiocarbamate ions is 1:5 to 5:1.

27. The process according to claim 14, wherein the aqueous solvent is water or water-based buffer.

28. The process according to claim 27, wherein the aqueous solvent is sterile.

29. The process according to claim 27, wherein the water-based buffer is selected from the group consisting of phosphate, citrate, acetate, Tris, HEPES, and saline buffers.

30. The molecular complex of dithiocarbamate-copper complex and at least one blood protein, obtainable by the process of claim 14.

31. A method of treatment comprising the step of administering a therapeutic comprising the molecular complex according to claim 1 to a subject in need thereof, wherein the treatment is selected from the group consisting of chemotherapy of cancer and radiotherapy of cancer.

32. The method of treatment according to claim 31, wherein the therapeutic agent is administered in a manner selected from the group consisting of parenterally, orally, and topically.

33. The method of treatment according to claim 31, wherein a concentration of bis(diethyldithiocarbamate)copper (CuET) in blood after 1 hour of injection administration is at least 1 ng/l or wherein a concentration of CuET in blood during infusion administration is at least 5 ng/1.

34. The method of treatment according to claim 31, wherein the molecular complex comprises immunoglobulin or immunoglobulin-containing blood protein mixtures as blood proteins, and further harbours antibodies or antibody fragments against tumour antigens or cell specific markers.

35. A method of visualization of tumors, comprising the steps of:

administering a diagnostic agent comprising the molecular complex according to claim 1 to a subject whose tumor is to be visualized, wherein the molecular complex contains radioactive isotopes of copper; and
visualizing the tumor.

36. The method of visualization according to claim 35, wherein the diagnostic agent is administered in a manner selected from the group consisting of parenterally, orally, and topically.

37. The method of visualization according to claim 35, wherein a concentration of bis(diethyldithiocarbamate)copper (CuET) in blood after 1 hour of injection administration is at least 1 ng/l or wherein a concentration of CuET in blood during infusion administration is at least 5 ng/l.

38. The method of visualization according to claim 35, wherein the molecular complex comprises immunoglobulin or immunoglobulin-containing blood protein mixtures as blood proteins, and further harbours antibodies or antibody fragments against tumour antigens or cell specific markers.

* * * * *